United States Patent
Gross et al.

(10) Patent No.: US 8,791,099 B2
(45) Date of Patent: Jul. 29, 2014

(54) TRANSITION METAL COMPLEXES OF CORROLES FOR PREVENTING CARDIOVASCULAR DISEASES OR DISORDERS

(75) Inventors: Zeev Gross, Petach Tikva (IL); Michael Aviram, Haifa (IL); Adi Haber, Haifa (IL); Bianca Fuhrman, Hiafa (IL); Atif Mahammed, Muawya Village (IL); Raymond Coleman, D.N. Menashe (IL)

(73) Assignee: Technion Research and Development Foundation Ltd., Haifa (IL)

( * ) Notice: Subject to any disclaimer, the term of this patent is extended or adjusted under 35 U.S.C. 154(b) by 1098 days.

(21) Appl. No.: 12/675,915

(22) PCT Filed: Aug. 4, 2008

(86) PCT No.: PCT/IL2008/001066
§ 371 (c)(1),
(2), (4) Date: Feb. 28, 2011

(87) PCT Pub. No.: WO2009/027965
PCT Pub. Date: Mar. 5, 2009

(65) Prior Publication Data
US 2011/0144078 A1    Jun. 16, 2011

Related U.S. Application Data

(60) Provisional application No. 60/968,416, filed on Aug. 28, 2007.

(51) Int. Cl.
*A61K 31/555* (2006.01)
(52) U.S. Cl.
USPC .......................................... 514/185; 514/824
(58) Field of Classification Search
None
See application file for complete search history.

(56) References Cited

U.S. PATENT DOCUMENTS

| | | | |
|---|---|---|---|
| 6,541,628 B1 | 4/2003 | Gross et al. | |
| 6,544,975 B1 | 4/2003 | Crapo et al. | |
| 6,939,963 B2 | 9/2005 | Gross et al. | |
| 2006/0003982 A1 | 1/2006 | Williams et al. | |

FOREIGN PATENT DOCUMENTS

| | | |
|---|---|---|
| FR | 2676738 A | 11/1992 |
| WO | WO9531197 A | 11/1995 |
| WO | WO0027379 A | 5/2000 |
| WO | WO0075144 A | 12/2000 |
| WO | WO03004021 A | 1/2003 |
| WO | WO2006037050 A | 4/2006 |

OTHER PUBLICATIONS

Gershman Z., Goldberg I., Gross Z. DNA binding and catalytic properties of positively charged corroles. Angew. Chem. Int.. Ed. 46, 4320-24 (2007).
Mahammed, A. and Gross, Z. Albumin-conjugated corrole metal complexes: extremely simple yet very efficient biomimetic oxidation systems. J Am Chem Soc 127, 2883-7 (2005).
I. Saltsman, A. Mahammed, I. Goldberg, E. Tkachenko, M. Botoshansky, and Z. Gross; "Selective Substitution of Corroles: Nitration, Hydroformylation, and Chlorosulfonation", J. Am. Chem. Soc., 124, 7411-7420 (2002).
Mahammed, A. and Gross, Z. Iron and manganese corroles are potent catalysts for the decomposition of peroxynitrite. Angew Chem Int Ed Engl 45, 6544-7 (2006).
Hunt, J. A., Lee, J. and Groves, J. T., Amphiphilic peroxynitrite decomposition catalysts in liposomal assemblies. Chemistry & Biology 4, 845-858 (1997).
German Camejo et al; "Hemin binding and oxidation of lipoproteins in serum: mechanisms and effect on the interaction of LDL with human macrophages", Journal of Lipid Research, vol. 39, pp. 775-766 (1998).
M. Kongsheug et al; "The distribution of porphyrins with different tumour localising ability among human plasma proteins", British Journal of Cancer, vol. 59, pp. 184-188 (1989).
P. Chris De Smidt et al "Properties of Incorporation, Redistribution, and Integrity of Porphyrin-Low-Density Lipoprotein Complexes", Biochemistry, vol. 32, pp. 2916-2922 (1993).

*Primary Examiner* — Savitha Rao
*Assistant Examiner* — Gregg Polansky
(74) *Attorney, Agent, or Firm* — Browdy and Neimark, PLLC

(57) ABSTRACT

Transition metal complexes of amphiphilic/bipolar corroles, optically active isomers or pharmaceutically acceptable salts thereof are useful for prevention of a cardiovascular disease or disorder in a subject susceptible to develop such a cardiovascular disease or disorder.

9 Claims, 10 Drawing Sheets

TRANSITION METAL COMPLEXES OF CORROLES FOR PREVENTING CARDIOVASCULAR DISEASES OR DISORDERS

FIELD OF THE INVENTION

The present invention relates to methods and compositions for treatment of cardiovascular diseases or disorders and, in particular, to such methods and compositions comprising a transition metal complex of a corrole.

BACKGROUND OF THE INVENTION

Corroles

Corroles are tetrapyrrole macrocycles that are closely related to porphyrins, with one carbon atom less in the outer periphery and one NH proton more in their inner core. The corroles are much less known than porphyrins and their synthesis was considered to be very complex. A simple procedure for corrole synthesis and their use as chemical catalysts have been disclosed in Gross et al. U.S. Pat. No. 6,541,628, assigned to the same applicant.

U.S. Pat. No. 6,730,666, in which the applicant is a co-assignee, discloses porphyrins and corroles useful for inhibition of cell proliferation mediated by growth factor receptor tyrosine kinase activity, for example, for inhibition of angiogenesis, or vascular smooth muscle cell proliferation in disorders including atherosclerosis, hypertrophic heart failure and postsurgical restenosis, and inhibition of cell proliferation and migration in the treatment of primary tumors and metastasis. The sole corrole disclosed in this patent was shown to inhibit the appearance of lung metastasis in an animal model.

New selectively-substituted corroles are disclosed in Gross et al. U.S. Pat. No. 6,939,963 assigned to the same applicant as well as their use for tumor detection and treatment, in photovoltaic devices, as catalysts and as intermediates.

The inventors have demonstrated in two recent publications that the iron and manganese complexes of 5,10,15-tris (pentafluorophenyl)-2,17-bis(sulfonic acid)-corrole disclosed in U.S. Pat. No. 6,939,963 are excellent catalysts for decomposition of two important reactive molecules, hydrogen peroxide ($H_2O_2$) and peroxynitrite (HOONO) (Mahammed et al., 2005; Mahammed and Gross., 2002). Firm evidence in favor of a disproportionation mechanism was provided for both $H_2O_2$ and HOONO: they first serve as oxidants for transferring the Mn(III) corrole into the (oxo)Mn (V) complex, which then utilizes the same molecules as reductants for returning to Mn(III). Less detailed mechanistic insight was obtained for the iron complex, but its catalytic rates were found to be faster than those of the Mn complex and it apparently induced isomerization rather than disproportionation of peroxynitrite. The fast action of the Fe complex and the unique mechanism adopted by the Mn complex suggest a significant added value of these complexes in the continuous efforts devoted to the development of synthetic catalysts that may either neutralize or avoid the formation of reactive oxygen and nitrogen species.

Besides being potent catalysts for decomposition of peroxynitrite in purely chemical systems, the above metallocorroles (of unique amphiphilicity and bipolarity due to the positioning of sulfonic acid head groups on the otherwise lipophilic corrole) were also shown to have large affinity to various proteins (Haber et al., 2008; Mahammed et al., 2004), a very important factor that may be used for selective delivery purposes.

Another publication by the inventors (Gershman et al., 2007) discloses DNA binding and catalytic properties of novel positively charged Mn complex of corrole containing pyridinium groups.

Cardiovascular Diseases and Disorders

Cardiovascular diseases and disorders involve the heart and/or blood vessels and include, for example, congestive heart failure (CHF) or heart failure, a condition in which the heart cannot pump enough blood to the body's other organs and may result from (i) narrowed arteries that supply blood to the heart muscle—coronary artery disease; (ii) past heart attack, or myocardial infarction, with scar tissue that interferes with the heart muscle's normal work; (iii) high blood pressure; (iv) heart valve disease due to past rheumatic fever or other causes; (v) primary disease of the heart muscle itself, called cardiomyopathy; (vi) congenital heart defects; (vii) infection of the heart valves and/or heart muscle itself, i.e., endocarditis and/or myocarditis.

Other cardiovascular diseases or disorders include myocardial infarction, the rapid development of myocardial necrosis that usually results from plaque rupture with thrombus formation in a coronary vessel, resulting in an acute reduction of blood supply to a portion of the myocardium; myocardial ischemia, a condition in which oxygen deprivation to the heart muscle is accompanied by inadequate removal of metabolites because of reduced blood flow or perfusion; and atherosclerosis.

Atherosclerosis is the leading cause of death in the developed world and is predicted to be the leading cause of death in the developing world. It is a chronic vascular disease characterized by cholesterol accumulation in the arterial wall, including macrophage foam cell formation, secondary to blood lipoproteins uptake. This disease may develop into a complete blockage of the arteries, resulting in a heart attack or a stroke. A major risk factor for the disease is high levels of blood cholesterol and the oxidation of low-density lipoproteins (LDL) (Aviram, 1995; Steinberg et al., 1989). Oxidized LDL is taken up by macrophages in the arterial wall in a non-controlled fashion, thus leading to the formation of cholesterol-loaded foam cells (Dhaliwal and Steinbrecher, 1999; Aviram, 1996), the hallmark of early atherosclerosis.

It has been shown that both the risk and the rate of development of atherosclerosis are increased in diabetics. A molecular mechanism providing a link between the two disorders was described by Griffin et al. (2001) who showed that glucose regulates expression of the macrophage scavenger receptor CD36 at the level of translation. The increased translation of macrophage CD36 transcript under high glucose conditions provides a mechanism for accelerated atherosclerosis in subjects with diabetes.

Oxidative Stress and Atherosclerosis

The imbalance between the production of reactive oxygen species (ROS) and reactive nitrogen species (RNS), and the ability of biological systems to readily detoxify the reactive intermediates (or easily repair the resulting damage) is commonly called oxidative stress. Accumulating strong evidence points towards the involvement of oxidative stress in neurodegenerative diseases (Alzheimer's, Parkinson's, and the like) and in the biological aspects of ageing, as well as in atherosclerosis development (Barber et al., 2006; Beal, 2002; Moreira et al., 2005; Stocker and Keaney, 2005).

Hydrogen peroxide ($H_2O_2$) and peroxynitrite (HOONO) are two representatives of ROS, with the latter also being an RNS. In addition to the intrinsic reactivity of hydrogen peroxide and peroxynitrite toward certain organic molecules, both of them are precursors for .OH radical and the latter, to $.NO_2$ radical as well. These radical species (and secondary radicals derived from them) are considered to be the main species that damage a very large variety of molecules, including those that are of vital importance for the health of the living systems (Halliwell and Gutteridge, 1999).

Antioxidants are substances that may protect lipoproteins, other biomolecules and cells from the damage caused by free radicals. Natural antioxidants include, for example, glutathione, vitamin C, vitamin E and punicalagin as well as enzymes such as catalase, superoxide dismutase, paraoxonases and various peroxidases. Paraoxonases are a group of enzymes involved in the hydrolysis of organophosphates. Paraoxonases 1 and 3 (PON1 and PON3) function as antioxidants, by preventing the oxidation of LDL, while paraoxonase 2 (PON2) can protect cells against oxidative damage. Punicalagins are large polyphenol tannins, which were found to be the major component responsible for pomegranate juice's antioxidant and health benefits.

The problem unique to peroxynitrite is that, in contrast to all other ROS and RNS and their precursors, there is no known biological defense system against it and most natural antioxidants are very poor scavengers of peroxynitrite (Bartletta et al., 1995; Szabó et al., 2007). This call for the development of synthetic molecules that could act on and neutralize peroxynitrite by one or more of the following ways: a) interfere with its formation by eliminating its precursors (superoxide anion and nitric oxide); b) decompose it to biologically benign products; c) repair the damage caused by it.

As mentioned above, we have shown that the iron and manganese complexes of 5,10,15-tris(pentafluorophenyl)-2, 17-bis(sulfonic acid)-corrole are excellent catalysts for decomposition of hydrogen peroxide and peroxynitrite (Mahammed et al., 2005; Mahammed and Gross., 2002).

SUMMARY OF THE INVENTION

It has now been found in accordance with the present invention that the iron complex of the amphiphilic/bipolar corrole, herein designated 1-Fe, is a highly potent catalyst for decomposition of reactive oxygen and nitrogen species that protects LDL and HDL against oxidation, binds to HDL/LDL with high selectivity, affects cholesterol level, as well as its cellular efflux. Due to the combination of these effects, mice consuming that complex were significantly saved from atherosclerosis development.

The present invention thus relates, in one aspect, to a method for prevention of a cardiovascular disease or disorder in a subject susceptible to develop said cardiovascular disease or disorder, which comprises administering to the subject an effective amount of a transition metal complex of an amphiphilic/bipolar corrole, an optically active isomer or a pharmaceutically acceptable salt thereof.

The cardiovascular disease or disorder includes, but is not limited to, atherosclerosis, congestive heart failure, myocardial infarction, myocardial ischemia and reperfusion.

In a preferred embodiment, the invention is directed to the prevention of atherosclerosis. Heart diseases may be related to complications related to diabetes. It has been established, for example, that both the risk and the rate of development of heart diseases including atherosclerosis are increased in diabetics. Thus, in an additional preferred embodiment, the invention is directed to the prevention of atherosclerosis in subjects suffering from diabetes.

In one embodiment, the amphiphilic/bipolar corrole metal complex of the invention has the formula I

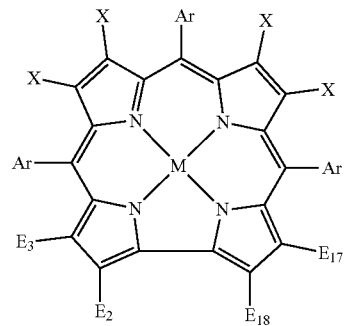

or a pharmaceutically acceptable salt or optically active isomer thereof, wherein:

Ar, the same or different, is an aryl selected from carboaryl, heteroaryl or mixed carboaryl-heteroaryl;

M is a transition metal selected from Mn, Fe, Ru, Co, V, Cr, Cu or Rh;

X is H or halogen;

$E_2$, $E_3$ and $E_{17}$, the same or different, each is H, halogen, $SO_2Cl$, $SO_3H$, $SO_2NR_1R_2$, $CO_2H$, $CO_2R$, COCl, $CONR_1R_2$, CHO, $CH=C(CO_2H)_2$, $CH=C(CN)CO_2H$), or $NO_2$, R is alkyl or aryl and $R_1$ and $R_2$, the same or different, each is H, alkyl, aryl or together with the N atom to which they are attached form a saturated 5-6 membered ring optionally containing a further heteroatom selected from O, S and N;

$E_{18}$ is H or CHO; or $E_3$ is H and $E_2$ and $E_{17}$ are each $SO_2$, both $SO_2$ groups being linked by a bridge $R_3N(R_4)$-phenyl-$(R_4)NR_3$, wherein $R_3$ is H, alkyl, phenyl or aralkyl, and $R_4$ is alkylene; and provided that at least one of $E_2$, $E_3$, $E_{17}$ and $E_{18}$ is not H.

In one preferred embodiment, the transition metal M is Fe. In another preferred embodiment, M is Mn.

In preferred embodiments, $E_2$ and $E_{17}$ are both —$SO_3H$ and each R is pentafluorophenyl or 4-methoxy-2,3,5,6-tetrafluorophenyl and the corrole complexes are 5,10,15-tris (pentafluorophenyl)-2,17-bis(sulfonic acid)-corrolato manganese(III) (herein designated 1-Mn), 5,10,15-tris (pentafluorophenyl)-2,17-bis(sulfonic acid)-corrolato iron (III) (herein designated 1-Fe), 5,10,15-tris(4-methoxy-2,3,5, 6-tetrafluorophenyl)-2,17-bis(sulfonic acid)-corrolato iron (III) (herein designated 2-Fe) or 5,10,15-tris(4-methoxy-2,3, 5,6-tetrafluorophenyl)-2,17-bis(sulfonic acid)-corrolato manganese (III) (herein designated 2-Mn).

In accordance with the present invention, the transition metal complexes of amphiphilic/bipolar corroles are capable of exhibiting one or more of the following activities: (i) they reduce blood cholesterol; (ii) they reduce oxidation of the low density lipoproteins (LDL) and high-density lipoproteins (HDL); (iii) they bind to LDL and HDL, predominantly to HDL, and may selectively be transported by the lipoproteins to the arterial wall; (iv) they bind to LDL and HDL particles in a number [40±5 and 10, respectively] higher than that of natural antioxidants (Esterbauer et al, 1989) [a mean of 9 for LDL and lower for HDL]; (v) they reduce the level of LDL (or its components or its activity); (vi) they increase the levels of HDL (or its components or its activity); (vii) they increase macrophage paraoxonase 2 (PON2) enzyme activity; (viii)) they increase serum and HDL-associated paraoxonase 1 (PON1) activity; (ix) they increase cholesterol, including serum-mediated cholesterol, efflux from macrophages; (x)

they decrease cholesterol synthesis by macrophages; and (xi) they can attenuate the formation of atherosclerotic lesions.

The invention further relates to a pharmaceutical composition for prevention of a cardiovascular disease or disorder comprising a pharmaceutically acceptable carrier and a transition metal complex of a corrole, preferably of the formula I hereinabove, or an optically active isomer or a pharmaceutically acceptable salt thereof.

The present invention still further relates to the use of a transition metal complex of a corrole, preferably of the formula I hereinabove, or an optically active isomer or a pharmaceutically acceptable salt thereof for the preparation of a pharmaceutical composition for prevention of a cardiovascular disease or disorder.

The present invention yet further relates to a transition metal complex of a corrole, preferably of the formula I hereinabove, or an optically active isomer or a pharmaceutically acceptable salt thereof for use in prevention of a cardiovascular disease or disorder.

BRIEF DESCRIPTION OF THE FIGURES

In FIG. 7A values are means±SEM, n=6, except for the 1-Fe group where the mean is calculated based on n=4, as two of the mice in the group did not show formation of an atherosclerotic lesion at all.

In FIG. 8B, values are means±SEM.

DETAILED DESCRIPTION OF THE INVENTION

Figure 1:
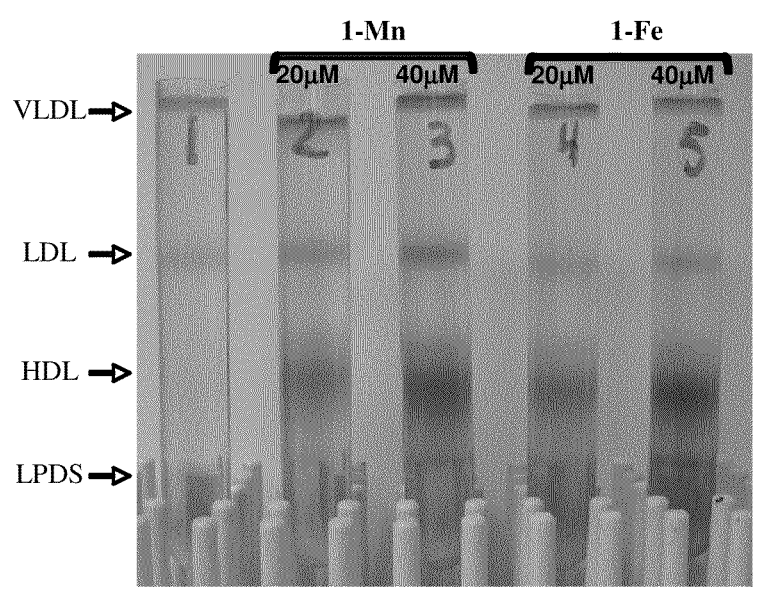
FIG. 1 shows a density gradient ultra centrifuged serum with (1) no additive, (2,3) 1-Mn, and (4,5) 1-Fe. The yellow rings are due to different serum fractions and the green color is due to the associated corroles.

The corroles of the formula I used in the present invention and the methods for their preparation are described in U.S. Pat. No. 6,939,963. They are water-soluble 5,10,15-triarylcorroles in which each aryl radical is selected from a carboaryl, a heteroaryl and a mixed carboaryl-heteroaryl radical and one to three of the positions 2, 3, 17 and 18 are substituted.

The radical Ar in the positions 5, 10 and 15 of I may be aryl or heteroaryl. As used herein, the term "aryl" refers to a carboaryl phenyl or naphthyl radical optionally substituted by one or more halogen atoms, or by one or more $C_1$-$C_6$ alkyl, $C_1$-$C_6$ alkoxy, nitro, hydroxy, amino, or pyridyl. Thus, Ar may, for example, be 2,6-dichlorophenyl, 2,6-difluorophenyl, pentafluorophenyl, 4-methoxy-2,3,5,6-tetrafluorophenyl. In one preferred embodiment, Ar is pentafluorophenyl. In another preferred embodiment, Ar is 4-methoxy-2,3,5,6-tetrafluorophenyl.

As used herein, the term "heteroaryl" refers to a 5-6 membered heteroaromatic radical containing one or more heteroatoms selected from O, S and/or N such as, but not being limited to, pyrryl, furyl, thienyl, oxazolyl, thiazolyl, pyridyl, and pirazinyl.

Examples of mixed carboaryl-heteroaryl radicals include 4-(pyridyl)-2,3,5,6-tetrafluorophenyl and 4-(N-methyl-pyridylium)-2,3,5,6-tetrafluorophenyl.

The Ar in positions 5, 10 and 15 may be identical or different aryl or heteroaryl radical. In one embodiment, the three Ar are identical and are 4-N-methylpyridylium. In another embodiment, Ar at positions 5 and 15 are 4-N-methylpyridylium and at position 10 Ar is pentafluorophenyl and M is preferably Mn (Gershman et al., 2007).

As used herein, the term "alkyl" alone or as part of a radical such as "aralkyl" or "alkylene" refers to a straight or branched $C_1$-$C_6$ alkyl radical such as, but not limited to, methyl, ethyl, propyl, isopropyl, butyl, pentyl and hexyl. The term "halogen" as used herein refers to fluoro, chloro, bromo or iodo.

In one embodiment of the invention, $E_2$ and $E_{17}$ are $SO_2Cl$ and $E_3$ and $E_{17}$ are hydrogen exemplified by the compound 2,17-bis(chlorosulfonyl)-5,10,15-tris(pentafluorophenyl) corrole.

In another embodiment of the invention, $E_2$ and $E_{17}$ are $SO_3H$ and $E_3$ and $E_{18}$ are hydrogen.

Also contemplated by the present invention are pharmaceutically acceptable salts of the corrole of formula I.

Pharmaceutically acceptable salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine (see, for example, Berge S. M., et al., "Pharmaceutical Salts," (1977) J. of Pharmaceutical Science, 66:1-19). The salts can also be pharmaceutically acceptable quaternary salts such as a quaternary salt of the formula —NRR'R"+Z' wherein R, R' and R" each is independently hydrogen, alkyl or benzyl and Z is a counterion, including chloride, bromide, iodide, O-alkyl, toluenesulfonate, methylsulfonate, sulfonate, phosphate, or carboxylate.

Pharmaceutically acceptable acid addition salts of the compounds include salts derived from inorganic acids such as hydrochloric, nitric, phosphoric, sulfuric, hydrobromic, hydriodic, phosphorous, and the like, as well as salts derived from organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate or galacturonate (see, for example, Berge S. M., et al., "Pharmaceutical Salts," (1977) J. of Pharmaceutical Science, 66:1-19).

In preferred embodiments, the compounds are 5,10,15-tris(pentafluorophenyl)-2,17-bis(sulfonic acid)-corrolato manganese(III), herein designated 1-Mn, and 5,10,15-tris(pentafluoro-phenyl)-2,17-bis(sulfonic acid)-corrolato iron(III), herein designated 1-Fe. The formulas of 1-Mn and 1-Fe as well as of 1-Ga prepared and used for comparison are depicted in Scheme 1 hereinafter just before the claims.

In other preferred embodiments, the compound is 5,10,15-tris(4-methoxy,2,3,5,6-tetrafluorophenyl)-2,17-bis(sulfonic acid)-corrolato iron(III), herein designated 2-Fe, or 5,10,15-tris(4-methoxy,2,3,5,6-tetrafluorophenyl)-2,17-bis(sulfonic acid)-corrolato manganese(III), herein designated 2-Mn. These compounds are novel and are encompassed as novel compounds by the present invention.

The disproportionation mechanism for catalytic decomposition of hydrogen peroxide and peroxynitrite by 1-Mn and the balanced equations for catalytic decomposition of peroxynitrite by 1-Mn and 1-Fe are depicted in Scheme 2 hereinafter just before the claims.

According to the present invention, it is shown that the iron-corrole 1-Fe rescues small molecules from ROS-induced oxidation more efficiently than the manganese complex 1-Mn, the opposite holds for arresting RNS-induced nitration and that 1-Fe and 1-Mn are anti- and pro-oxidants, respectively, with regard to their in vitro effects on oxidative damage to LDL/HDL. An important finding regarding targeting is that both metallocorroles, as well as the non-transition metal complex 1-Ga, bind to lipoproteins stronger than to all other serum components. The only case where 1-Mn was superior to 1-Fe was in the systems designed to test the ability of the catalysts to avoid formation of nitrating species, i.e., the nitration of tyrosine and fluorescein. This is perfectly consistent with the mode of action of the former complex on peroxynitrite, as dilute nitrite obtained from 1-Mn is not a nitrating agent while nitrate (from the action of 1-Fe) is. On the other hand, both complexes served equally well for rescuing DMSO and deoxyribose from reacting with hydroxyl radical that is otherwise produced from the spontaneous (non-catalyzed) decomposition of peroxynitrite. The only case where both complexes were not perfect inhibitors was the sulfoxide to sulfone oxidation, which is most likely to be an oxygen atom transfer reaction. Nevertheless, the amount of oxidation product was significantly reduced in the presence of the metallocorroles, with better results observed with 1-Fe. Since most results for induced damage to LDL were obtained with $CuSO_4$ as the initiator of reactive oxygen species, this system was also tested on DMSO. In this case, a reducing agent (ascorbate) was added for inducing the complex Fenton-type oxidation that produces hydroxyl radical via the involvement of superoxide anion radical and hydrogen peroxide. 1-Fe eliminated the oxidation of DMSO to malonyldialdehyde (MDA) completely and 1-Mn only partially, consistent with the faster decomposition of hydrogen peroxide by 1-Fe relative to 1-Mn. These investigations clearly point toward the following conclusions: both complexes serve very well for avoiding the formation of hydroxyl radical from peroxynitrite; the iron complex is more efficient in avoiding the formation of metal-induced hydroxyl radical; the manganese complex is more efficient in avoiding the formation of reactive nitrogen species from peroxynitrite For evaluation of the effect of corroles on LDL oxidation induced by peroxynitrite the reagent SIN-1, that slowly produces peroxynitrite, was applied. The formation of conjugated dienes, the preliminary step in fatty acid oxidation, was followed upon addition of SIN-1 in the presence or absence of corroles. While 1-Mn was found to be a pro-oxidant, increasing both the rate of formation and the amount of conjugated dienes, 1-Fe was an excellent anti-oxidant totally preventing conjugated dienes formation.

For copper-induced LDL oxidation, formation of conjugated dienes (CD), fatty acid peroxides (PD) and thiobarbituric acid reactive substances (TBARS) were measured. The aforementioned indications pointing toward pro-oxidant activity of 1-Mn and anti-oxidant activity of 1-Fe gained highly significant supporting evidence from these experiments. In fact, the results disclosed herein are unmatched by any previously reported metal complexes, as 1-Fe exhibited full inhibition at concentrations as low as 2.5 µM, and especially in light of what is known on porphyrin complexes.

Comparison of 1-Fe to results obtained with porphyrins shows its superiority as follows: Pyridinium-substituted positively charged manganese porphyrins play a pro-oxidative role when oxidizing LDL with peroxynitrite, and only in the presence of reductants such as uric acid they shift to an anti-oxidative role (Trostchansky et al., 2003). The concentration needed for 100% inhibition of oxidation is 100 µM (Day et al., 1999), 40 times more than 1-Fe concentration needed for full inhibition. In addition, these complexes do not inhibit copper induced LDL oxidation (Bloodsworth et al., 2000). On the other hand, iron porphyrins do not display potency for inhibiting LDL oxidation at all (Day et al., 1999), and hemin is frequently used as means for initiation of LDL oxidation rather than inhibition (Camejo et al., 1998; Kapiotis et al., 2005).

Oxidation of HDL in a copper-induced system gave very similar results to those obtained for LDL, with 1-Mn again being a pro-oxidant and 1-Fe an anti-oxidant. The main difference was the lower total damage, which is obviously due to the lower lipid content of HDL relative to LDL.

All three corroles also affect cholesterol levels and distribution in plasma; and 1-Fe, but not 1-Mn or 1-Ga, increases cellular efflux of cholesterol from macrophages.

Since high levels of blood cholesterol and the oxidation of low-density lipoproteins are considered to be major risk factors for the development of atherosclerosis and the corroles of the invention are shown herein to reduce these risk factors, an animal study was performed on apolipoprotein E deficient mice ($E^0$ mice prone to develop atherosclerosis) to evaluate the efficacy of these corroles to prevent the disease. The histopathological development of lesions in the aorta was very high for untreated mice and for those that received 1-Ga in their drinking water. In contrast, quite a significant decrease (relative to the control group) in the average lesion area was obtained for the 1-Mn group, despite of the above mentioned in vitro indications of a pro-oxidant activity for this complex. But, the in vivo results obtained with 1-Fe were completely consistent with all other results and much out of the range of statistical uncertainty. These observations are much better than those obtained by other methods, including $E^0$ mice that were treated by natural anti-oxidants (48% reduction when consuming red wine (Hayek et al., 1997; Fuhrman et al., 1995) and 44% for pomegranate juice (Aviram et al., 2000)) or those that were IP-treated with different synthetic catalysts for decomposition of reactive oxygen species. In fact, we are not aware of any report where a positive effect of orally administrated synthetic anti-oxidants displayed such a positive effect on postponing or eliminating the development of atherosclerosis. The iron complex is more effective than natural anti-oxidants for attenuation of atherosclerosis development in mice, attributable to the synergetic effects that were deduced from the in vitro investigations.

The mice were also examined with regard to the levels of total serum cholesterol and the macrophage paraoxonase 2 (PON2) lactonase activity, two factors relevant to the development of atherosclerosis. High cholesterol level is considered as one of the most common risk factors contributing to atherosclerosis, while PON2 is an enzyme acting as an antioxidant in the cellular level, and it has been found that cells overexpressing PON2 are less able to oxidize LDL (Ng et al., 2001). The total serum cholesterol values in mice that received 1-Fe was lower by 40% than in the control group; and significant reductions was also noted in the mice that received 1-Mn and 1-Ga. Examination of PON2 activity revealed an increase in PON2 lactonase activity versus the control mice in all mice groups receiving corrole derivatives. The combination of low cholesterol values and increases PON2 lactonase activity may explain why 1-Mn displayed a positive effect in the in vivo investigations, despite of the discouraging in vitro results.

The observations obtained in the mice model of atherosclerosis appear to be very much consistent with the in vitro results, which disclosed that the iron complex 1-Fe is a very potent catalytic antioxidant that also affects cholesterol efflux from macrophages and lowers LDL's cholesterol levels. The unique bipolarity of corrole 1 is apparently responsible for the selective binding to lipoproteins, which is very important for their protection from oxidative damage and may serve as a mechanism for delivering the complexes to the arterial wall. This, together with the very fast catalytic rates of 1-Fe, is of particular relevance in the context of the comparison with dietary antioxidants: the non-catalytic activity of polyphenols was shown to occur at concentrations at least one order of magnitude higher than their bioavailability (Ferroni et al., 2004).

The corrole iron complex 1-Fe was more efficient in inhibiting the oxidation of small molecules induced by peroxynitrite and by copper ions, while the manganese complex was more efficient in preventing the formation of reactive nitrogen species 1-Mn from peroxynitrite. Exceptionally low concentrations of 1-Fe provided complete protection against the in vitro oxidation of LDL by either peroxynitrite or copper ions, while 1-Mn displayed a pro-oxidative role under these conditions. The in vivo effects of the corroles on atherosclerotic mice were most novel. Oral administration of 0.2 mg/day dosages of 1-Fe led to a highly remarkable attenuation of lesion formation, with two of the six mice not developing any atherosclerotic lesions at all and the other four mice developing average lesion area that were 60% smaller than for control mice. Quite significant decreases in serum cholesterol levels and increases in macrophage PON2 activity were obtained for both 1-Fe and 1-Mn, which together with the possible inhibition of nitration, could explain the partial (and surprising) attenuation of lesion formation seen in mice treated with 1-Mn.

The fast action of 1-Fe and the unique mechanism adopted by 1-Mn suggest a significant added value of these complexes in the continuous efforts devoted to the development of synthetic catalysts that may either neutralize or avoid the formation of reactive oxygen and nitrogen species. In addition to the intrinsic reactivity of hydrogen peroxide and peroxynitrite toward certain organic molecules, both of them are also precursors to .OH and the latter to $.NO_2$ as well. These radical species (and secondary radicals derived from them) are considered the main species that damage a very large variety of molecules, including those that are of vital importance for the health of living systems.

The pharmaceutical compositions of the present invention comprising metal complexes of corroles are formulated for administration to the patient using techniques well-known in the art, for example, as summarized in Remington's Pharmaceutical Sciences, Mack Publishing Co., Easton, Pa., latest edition.

In a preferred embodiment, the pharmaceutical composition for use in the present invention is administered parenterally.

In one more preferred embodiment, the pharmaceutical composition for use in the present invention is administered orally. As far as known to the inventors, this is the first time that oral administration of a corrole is reported. The doses will depend on the type of disease or disorder and condition and age of the patient and may vary between 0.1 to 10 mg/kg/day.

The invention will now be illustrated by the following non-limiting examples.

EXAMPLES

Materials and Methods

Chemicals.

The corrole metal complexes and peroxynitrite solutions (freshly prepared on the day of usage) were prepared according to procedures previously disclosed by the inventors (U.S. Pat. No. 6,939,963; Mahammed and Gross, 2006; Saltsman et al., 2002; Hunt et al., 1997), while the solvents and standard chemicals were purchased from reliable sources and used as received. This includes SIN-1 (3-morpholinosydnonimine hydrochloride), EDTA, $CuSO_4$, thiobarbituric acid and folin reagent that were purchased from Aldrich. PBS (phosphate buffered saline) was purchased from Biological Industries. LDL was separated from plasma of normal healthy volunteers by sequential ultracentrifugation (Aviram, 1983) and dialyzed against saline with EDTA (1 mmol/L). LDL protein concentration was determined with the Folin phenol reagent (Lowry et al., 1951). Before the oxidation study, LDL was diluted in PBS to 1 g protein/L and dialyzed overnight against PBS at 4° C. to remove the EDTA.

(i) Oxidation of Small Molecules by Peroxynitrite a) Formaldehyde from DMSO: 1 mL of an aqueous solution containing NaOH (0.05 M) and peroxynitrite (2.5 mM)

was added to a 1 mL phosphate buffer solution that contained 20 μL DMSO and either no additive or 1-Fe (160 μM) or 1-Mn (160 μM). The final pH of the solutions was 7.4 and the temperature was maintained at 24° C. After 5 min of stirring, a 0.3 ml NaOH solution (7.8 M) was added to each tube for analyzing the amount of formed formaldehyde. This was immediately followed by supplying the tubes with 0.3 mL of 34.2 mM Purpald® (a color forming reagent for the determination of aldehydes; Aldrich Chemical Co.) in 480 mM HCl; and a second incubation with continuous shaking was performed for 10 min at 24° C. The thus obtained reaction product between formaldehyde and Purpald® was oxidized to a colored compound by the addition of 0.3 mL 470 mM $KIO_4$ in 470 mM NaOH. The absorbance at 550 nm was measured with a spectrophotometer and the amount of formaldehyde was determined by using a standard curve obtained from formaldehyde solutions of known concentrations (a linear curve was obtained by drawing final O.D. at 550 nm versus initial formaldehyde concentrations).

b) Malonyldialdehyde (MDA) from deoxyribose: 10 mM of deoxyribose in buffer solution was reacted with 390 μM of peroxynitrite in both the absence and the presence of 0.1 mM 1-Fe or 1-Mn (pH 7.4, T=24° C.). 1 mL of 2.8% trichloroacetic acid and 1 mL of 1% thiobarbituric acid in 0.1 M NaOH adjusted to pH 3.5 were sequentially added to 1 mL samples and the absorbance spectra at 532 nm due to the absorbance maximum of the MDA-thiobarbiturate product were recorded as a function of time (0-22 hr) at 24° C.

c) Sulfolane from tetramethylene sulfoxide: Peroxynitrite (6 mM) was added to a solution of tetramethylene sulfoxide (0.038 mM) in phosphate buffer solution pH 7.4 and T=25° C., both in the presence and absence of 38 μM 1-Fe or 1-Mn. The sulfolane was extracted into diethyl ether after 10 min of stirring and quantified by GC analysis. The same experiment was done at pH 12.7, with a reaction time of 4 hr.

d) Nitration of fluorescein: 5 μM of fluorescein in buffer was reacted with 25 μM of peroxynitrite in both the absence and the presence of 5 μM of 1-Fe or 1-Mn (T=24° C., pH 7.4). The changes in fluorescein absorbance were measured on the UV/vis spectrophotometer. The yield of nitration was determined by converting absorbance to changes in concentration of fluorescein and nitrated fluorescein, using pre-determined extinction coefficients. For increased accuracy, the three wavelengths in which the largest changes in absorbance occur were used. The yields were calculated based on the initial substrate concentration.

e) Nitration of L-tyrosine: Peroxynitrite (0.44 μmol) was reacted with 0.16 μmol of L-tyrosine in 2 mL phosphate buffer solution, pH 7.4 at T=24° C. for 5 min. The concentration of such formed nitrotyrosine was estimated by recording the 438 nm absorbance ($\epsilon$=4200 $M^{-1}cm^{-1}$) of basified solutions (via the addition of 0.2 ml of 7.8 M NaOH). The same experiments were repeated in the presence of either 0.1 μmol 1-Fe or 1-Mn.

f) Oxidation of DMSO by copper sulfate: DMSO (20 μt) was added to 2 mL phosphate buffer (pH 7.0, T=24° C.) in both the absence and the presence of 50 μM 1-Fe or 1-Mn. Reaction was initiated by adding a mixture of $CuSO_4$ and phenanthroline (final concentration of 8 μM for each), followed by sodium ascorbate (500 μM). After 18 hr of stirring, the amount of produced formaldehyde was assayed by reaction with Purpald® as described above.

The same experiment was done with glutathione instead of sodium ascorbate as reducing agent. The concentrations of the reagents were: 1 mM glutathione, 32 μM $CuSO_4$, 32 μM phenanthroline, 50 μM 1-Fe, 50 μM 1-Mn.

(ii) LDL/HDL Preparation:

LDL/HDL was separated from plasma of normal healthy volunteers by sequential ultracentrifugation (Aviram, 1983) and dialyzed against saline with EDTA (1 mM), Protein concentration of the separated fraction was determined with the folin phenol reagent. Before the oxidation study, LDL/HDL was diluted in PBS to 1 g protein/L and dialyzed against PBS at 4° C. to remove the EDTA.

(iii) Interaction of LDL [HDL] with Corroles:

The association between corroles and LDL was examined by recording the absorbance spectrum of 10 μM aqueous corrole 1-Mn, 1-Fe and 1-Ga PBS solutions before and after addition of 100 mg of LDL protein/L (corresponding to a molar concentration of 0.2 μM). The solutions where extensively dialyzed against PBS, and the electronic spectrum was measured again. The difference in the absorbance can be used to calculate the number of corrole molecules bound to LDL [HDL].

(iv) Corrole Distribution in Plasma:

The distribution of corroles in plasma was evaluated by adding either 20 or 40 μM of 1-Mn or 1-Fe to 4 mL plasma from healthy volunteers. After 30 minutes of equilibration, the mixtures were treated for 48 hours by ultracentrifugation in a KBr density gradient as previously described (Aviram et al., 2001). Fractions of VLDL, LDL, HDL and LPDS were collected, and the electronic spectrum recorded for identifying the presence of the corroles. Plasma fractions without corroles were used as reference. The amount of cholesterol in the fraction was determined by CHOL/PAP kit (Roche/Hitachi) and normalized according to fraction volume.

(v) Oxidation of LDL by Peroxynitrite:

LDL (100 mg protein/L) in PBS was incubated for 30 min at room temperature with or without 1-Mn, 1-Fe and 1-Ga (5 μM). LDL oxidation was induced by addition of SIN-1 (250 μM) and incubation for 4 hour at 37° C. under air in a PowerWave$_x$ Microplate Scanning Spectrophotometer (Bio-Tek Instruments Inc.) equipped with a KC4 software. LDL oxidation was continuously monitored by measuring the formation of conjugated dienes, as indicated by the increase in absorbance at 234 nm (Esterbauer et al., 1989).

(vi) Oxidation of LDL/HDL by Copper Sulfate:

LDL/HDL (100 mg protein/L) in PBS was incubated for 30 min at room temperature with or without 1-Mn, 1-Fe and 1-Ga at various concentrations (0.5, 2.5 and 5 μM). Oxidation was initiated by addition of a freshly prepared $CuSO_4$ solution (5 μM) and incubation at 37° C. under air in a shaking water bath was continued for 2 h (LDL) or 5 h (HDL). Lipoprotein oxidation was determined by measuring the amount of TBARS (Aviram et al. 2001).

Kinetic measurements were done in a similar manner with or without 2.5 μM 1-Mn or 1-Fe. Conjugated dienes formation was continuously monitored for 165 min while TBARS and lipid peroxides (Aviram et al. 2001) were measured after 15, 30, 45, 60, 75, 90, 120 and 165 minutes.

(vii) Corrole-Mediated Efflux from J-774 Macrophages:

Murine J-774 cells (1×10⁶/mL) were plated in 24-well plates for 24 hours, then washed and incubated for 1 hour in serum-free DMEM that contained ³H-cholesterol (2 μCi/mL) and BSA (0.2%). Cells were washed to remove unincorporated label and then incubated in 1 mL of DMEM without any additive or with 10, 25 or 50 μM of 1-Mn, 1-Fe or 1-Ga. After a 4-hour incubation at 37° C. to permit efflux of ³H-cholesterol from the cells into the medium, 500 μL of the medium was collected. The cells were washed with PBS, 1 mL of 0.1 N NaOH was added to the cells and 500 μL was collected the next day. Medium and cellular ³H-cholesterol were determined by liquid scintillation counting (LSC). The percentage of cholesterol efflux was calculated as the ratio of total counts per minute in the medium divided by the total counts per minute in the medium and in the cells. Corrole-mediated cholesterol efflux was calculated after subtraction of the non-specific efflux obtained in cells incubated in the absence of corroles.

(viii) Experiments with $E^0$ (Apolipoprotein E Deficient) Mice a) For atherosclerosis evaluation: At an age of about 10 weeks, 24 $E^0$ mice were randomly divided into 4 groups of 6 mice each. The groups differed only in the type of drinking water: no additive, and water containing 0.04 mM of either 1-Mn, 1-Fe or 1-Ga. Fluid consumption by the groups receiving 1-Mn and 1-Ga was ~5 mL/mouse/day, which equals to 0.2 mg per mouse per day. The group receiving 1-Fe was found to drink somewhat larger amounts (~6 mL/mouse/day). After 10 weeks the mice were sacrificed and blood samples, heart with attached aorta and mouse peritoneal macrophages (MPM) were collected from all mice.

b) For cholesterol efflux and cholesterol synthesis measurements: At an age of 10 weeks, 36 $E^0$ mice were divided randomly into 3 groups of 12 mice each. The groups differed only in the type of drinking water: no additive, and water containing 0.04 mM of either 1-Fe or 2-Fe (8 mg/Kg/day). After 14 weeks the mice were sacrificed and blood samples and mouse peritoneal macrophages (MPM) were collected from all mice. The blood samples from all mice in the same group were mixed and further fractionated in a KBr gradient to provide the pure HDL.

(ix) Serum Lipids (from viii, a):

Samples from all mice in the same group were mixed and analyzed for total cholesterol by CHOL/PAP kit (Roche Diagnostics) at the "chemistry laboratory" of Rambam Medical Center, Haifa.

(x) Macrophage Paraoxonase 2 (PON2) Activity (from viii,a):

Mouse peritoneal macrophages (MPM) were harvested 4 days after intraperitoneal injection of 3 mL thioglycolate (40 g/L). The cells were washed with PBS at 1000 g for 10 min, diluted to $10^6$ cells/mL in DMEM supplemented with fetal calf serum, plated and incubated at 5% $CO_2$ and 37° C. Dihydrocoumarin was utilized as substrate for measuring PON2 lactonase activity (Rosenblat, 2003). The cells ($2 \cdot 10^6$) were washed and incubated with 1 mL of 1 mM dihydrocoumarin in Tris buffer. After 10 min incubation at room temperature, the absorbance at 270 nm was measured. The self-hydrolysis of dihydrocoumarin was measured (and subtracted) under the same conditions in a cell-free system for calculating the cell-mediated hydrolysis of dihydrocoumarin.

(xi) Histopathology of Aortic Atherosclerosis Lesions (from viii,a):

At the end of the experiment, the mice were sacrificed and each heart and entire aorta were rapidly dissected out from each mouse and immersion-fixed in 3% glutaraldehyde in 0.1 mol/L sodium cacodylate buffer with 0.01% calcium chloride, pH 7.4, at room temperature. The first 4 mm of the aortic arch was stained with osmium tetroxide, which colors all the lipid components a dark brown-black color thus enabling delineation of the lesion with greater accuracy. The blocks were embedded in epon resin and thin transverse sections were cut to allow greater resolution of the lesion details. The area covered by the lesion was determined by image analysis (Coleman et al., 2006).

(Xii) Paraoxonase 1 (PON1) Activity (from viii,b):

Serum and HDL-associated PON1 activity towards phenylacetate (arylesterase activity) was measured spectrophotometrically at 270 nm. The assay mixture included 1.0 mmol/L of phenylacetate and 1.0 mmol/L $CaCl_2$ in 20 mmol/L Tris-HCl, pH 8.0, at 25° C. The $E_{270}$ for the reaction is 1310 $(mol/L)^{-1}$ $cm^{-1}$.

(xiii) Cholesterol Efflux by Mice Serum (from viii,b):

J-774 macrophages were incubated with [$^3$H]-labeled cholesterol for 1.5 h at 37° C. followed by cell wash in ice-cold PBS (3×) and further incubation in the presence of 15 µL mice serum for 3 h at 37° C. Cellular and medium [$^3$H]-labels were quantitated and HDL-mediated cholesterol efflux was calculated as the ratio of [$^3$H]-label in the medium/[$^3$H]-label in the medium+[$^3$H]-label in cells.

(xiv) Cholesterol Efflux from MPM (from viii,b):

Mouse peritoneal macrophages were incubated with [$^3$H]-labeled cholesterol for 1 h at 37° C. followed by cell wash in ice-cold PBS (3×) and further incubation in the absence or presence of 100 µg of human HDL protein/ml for 3 h at 37° C. Cellular and medium [$^3$H]-labels were quantitated and HDL-mediated cholesterol efflux was calculated as the ratio of [$^3$H]-label in the medium/[$^3$H]-label in the medium+[$^3$H]-label in cells.

(xv) Cholesterol Synthesis (from viii,b):

Cellular cholesterol biosynthesis was assayed after incubation of macrophages ($3 \times 10^6$ well$^{-1}$) overnight with DMEM containing 2% BSA followed by additional 3 h of incubation at 37° C. with [$^3$H]-acetate (3.3 µCi/ml). Cellular lipids were extracted with hexane:isopropanol (3:2, v:v), and the upper phase was dried under nitrogen. The lipids were then separated by TLC using an eluent of hexane:ether:acetic acid (130:30:1.5, v:v:v). Unesterified cholesterol spots were visualized by iodine vapor (by using standard for identification) and counted with β-counter.

Example 1

The Corrole Metal Complexes Prevent Oxidation and Nitration of Small Molecules by ROS and RNS Table 1 summarizes the results obtained by treating five different molecules with peroxynitrite, with and without catalytic amounts of 1-Fe or 1-Mn. These particular molecules were specifically chosen because they represent targets of hydroxyl radical, nitrogen dioxide, and of oxygen transfer reagents. In addition, their reaction products are easily identified and quantified by established methods.

TABLE 1

Oxidation of small molecules by peroxynitrite (PN).

|  |  |  | PN | PN + 1-Mn | PN + 1-Fe |
|---|---|---|---|---|---|
| (•OH) |  |  |  |  |  |
| 1) | DMSO→ | Formaldehyde | 11.5% | 0% | 0% |
| 2) | Deoxyribose→ | Malonyldialdehyde | 1.7% | 0% | 0% |

TABLE 1-continued

Oxidation of small molecules by peroxynitrite (PN).

| | | PN | PN + 1-Mn | PN + 1-Fe |
|---|---|---|---|---|
| ($^+NO_2$) | | | | |
| 3) Fluorescein→ | Nitrofluorescein | 30%[a] | 0% | 4%[a] |
| 4) L-Tyrosine→ (O) | L-Nitrotyrosine | 11% | 0% | 11% |
| 5) Tetramethylenesulfoxide→ | Sulfolane | 3.14% | 0.18% | 0.1% |
| | | 83%[b] | 0.6%[b] | 0.4%[b] | pH 7.4, T= 25° C., the yeilds relative to [PN]$_0$.
[a]Relative to [fluorescein]$_0$
[b]pH 12.7

The results were very illuminative: both complexes rescued the simple molecule DMSO, as well as the more sophisticated one, deoxyribose, from peroxynitrite-derived hydroxyl radical. The situation with regard to nitration by reactive nitrogen species originating from peroxynitrite was quite different: 1-Mn completely eliminated the reactions of both relevant molecules, while 1-Fe had no effect on the nitration of tyrosine, and was only partially effective in avoiding that of fluorescein. This is perfectly consistent with the mode of action of the complexes on peroxynitrite, as dilute nitrite obtained from 1-Mn (Scheme 2, equation 2) is not a nitrating agent while nitrate (from the action of 1-Fe, Scheme 2, equation 1) is.

Both complexes were quite (but not absolutely) effective with regard to arresting the oxidation of tetramethylenesulfoxide to sulfone, in a way which is most likely an oxygen atom transfer reaction, with 1-Fe displaying some larger efficiency. Additional experiments were carried out by using CuSO$_4$/ascorbate as the initiator of reactive oxygen species (by the complex Fenton-type oxidation that produces hydroxyl radical via the involvement of superoxide anion radical and hydrogen peroxide), as to bridge between the results of the small molecules and those obtained by oxidation of LDL. 1-Fe eliminated the oxidation of DMSO to malonaldehyde completely and 1-Mn did it only partially (65% inhibition), which is consistent with the faster decomposition of hydrogen peroxide by 1-Fe relative to 1-Mn.

These investigations clearly point toward the following conclusions: a) both complexes serve very well for preventing the formation of hydroxyl radical from peroxynitrite; b) the iron complex is more efficient in avoiding the formation of metal-induced hydroxyl radical; c) the manganese complex is more efficient in inhibiting the formation of reactive nitrogen species from peroxynitrite.

Example 2

Comparison of the Ability to Decompose Peroxynitrite of the Corrole Metal Complexes with the Punicalagin For initial assessment of possible superiority of the metallocorroles relative to natural antioxidants, we have determined the effect of excess (45-135 μM) punicalagin—the active polyphenolic hydrolysable tannin ingredient of pomegranate juice (Tzulker et al., 2007), on decomposition of peroxynitrite (40 μM). This information, together with the previously determined rate constants for catalytic decomposition of peroxynitrite (385 μM) by 1-Fe and 1-Mn (5-20 μM) (Scheme 2) (Mahammed et al., 2006; Gershman et al., 2007), were used for calculating the minimal concentrations required for reducing the half lifetime of peroxynitrite by 50%. The results revealed that 250 mol % punicalagin, 2.5 mol % 1-Mn, and 0.05 mol % 1-Fe are needed for that purpose, i.e., that the catalytically acting 1-Fe and 1-Mn are 5000 and 100 times, respectively, more effective than the most potent dietary antioxidant, pomegranate punicalagin, that acts in a sacrificial mode (i.e., being irreversibly oxidized instead of the more important biomolecule).

Example 3

The Corrole Metal Complexes Bind Preferably to Lipoproteins, Mainly to HDL

Possible interactions between the corroles and LDL were investigated prior to the examinations of the effect of the corroles on LDL oxidation. This was performed by recording the absorbance spectrum of 10 μM aqueous corrole solutions before and after addition of 100 mg of LDL protein/L (corresponding to a molar concentration of 0.2 μM). Large changes were induced upon the addition of LDL, with the most significant changes being shifts of absorbance maxima from 480 to 475 nm for 1-Mn, from 404 to 410 nm for 1-Fe, and from 424 to 428 nm for 1-Ga (which serves as a control for the two other corroles). These solutions ([LDL]/[corrole]=50) were dialyzed, and the absorbance after dialysis decreased by 20, 10 and 30% for 1-Mn, 1-Fe and 1-Ga respectively, leading to the conclusion that each LDL particle binds 40±5 corrole molecules with high affinity. This large number is quite reasonable since the LDL particle is very large and may not encompass specific binding sites, but rather the amphiphilic nature of the examined corroles renders them ideal for positioning in the phospholipid monolayer of the LDL, with the hydrophilic head groups sticking out toward the aqueous phase, as previously proposed for amphiphilic porphyrins (Camejo et al., 1998; Bonneau et al., 2004). In any case, no corrole is expected to be free in solution at the maximal corrole concentration used in the forthcoming experiments, namely, 5 μM per 100 mg of LDL protein/L (about 25 corrole molecules per LDL particle). Similar investigations with HDL revealed that each particle binds 10 corrole molecules with high affinity.

Treatment of 4 mL human serum with 1-Mn, 1-Fe and 1-Ga (20 and 40 μM concentrations were checked) and subsequent ultracentrifugation in KBr density gradient for 48 h revealed that the majority of the corroles (65-70%) accumulated in the fraction containing HDL and some in the LDL on the expense of all serum proteins (FIG. 1). Even dialysis (Mw=12,000-14,000, against PBS) of the isolated fractions left most of the corroles bound to the lipoproteins. These results suggest that the lipoproteins might carry the metallocorroles all the way to the arterial wall—where the antioxidant properties of the latter are needed.

Example 4

The Corrole Metal Complexes Prevent LDL/HDL Oxidation

Figure 2:
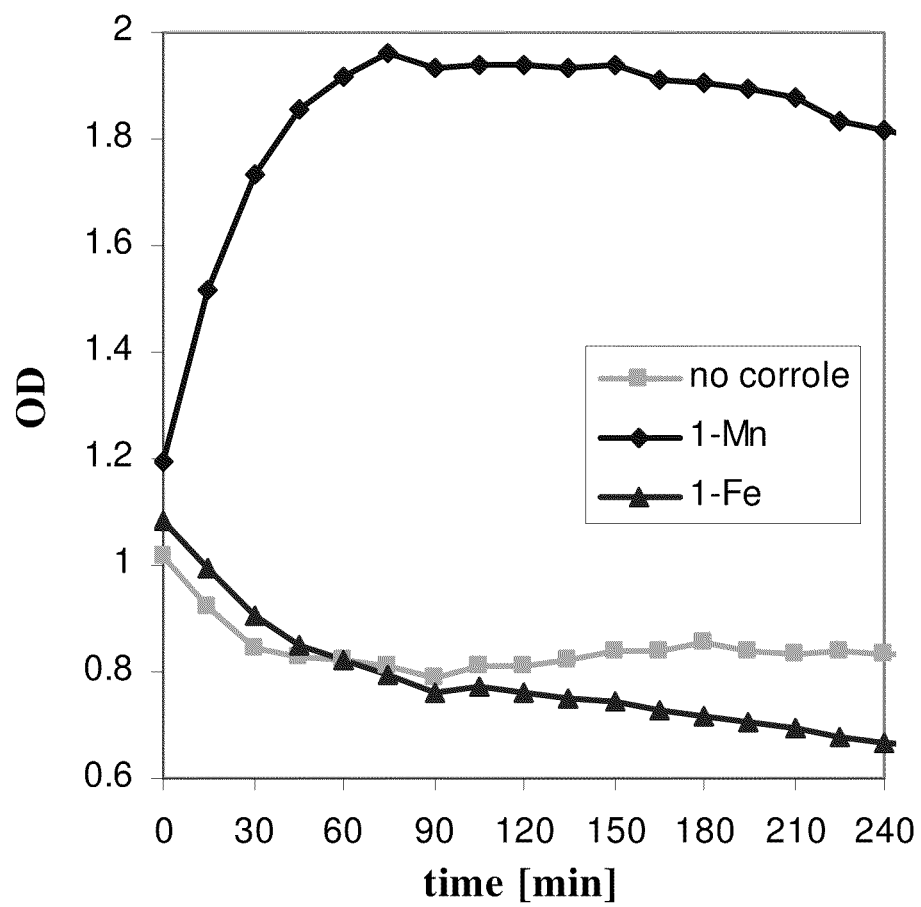
FIG. 2 shows the effect of corrole 1-Mn and 1-Fe on SIN-1 induced low-density lipoproteins (LDL) oxidation: ⋯✧⋯ without corrole; ⋯♦⋯ with 5 μM 1-Mn; and ⋯▲⋯ with 5 μM 1-Fe. LDL (100 g protein/L) was incubated with SIN-1 (250 μM) with or without corroles, and oxidation was monitored by following the absorbance at 234 nm.

For evaluation of the effect of corroles on LDL oxidation induced by peroxynitrite the reagent SIN-1 was applied. This reagent slowly produces nitric oxide and superoxide anion in proximity to one another, and thus leads to the formation of peroxynitrite. This slow introduction of peroxynitrite is believed to be a more physiological situation resembling the time-dependent formation of peroxynitrite (Thomas et al., 1998). The formation of conjugated dienes was followed upon addition of 250 µM SIN-1 and in the presence or absence of corroles (FIG. 2). Conjugated dienes formation represents an early stage of lipid peroxidation, where isomerization of isolated to conjugated fatty acid double bonds occurs due to the formation of a carbon-centered radical by the action of the reactive species. While 1-Mn was found to be a pro-oxidant, increasing both the rate of formation and the amount of conjugated dienes, 1-Fe was an excellent anti-oxidant totally preventing conjugated dienes formation.

Figure 3A:
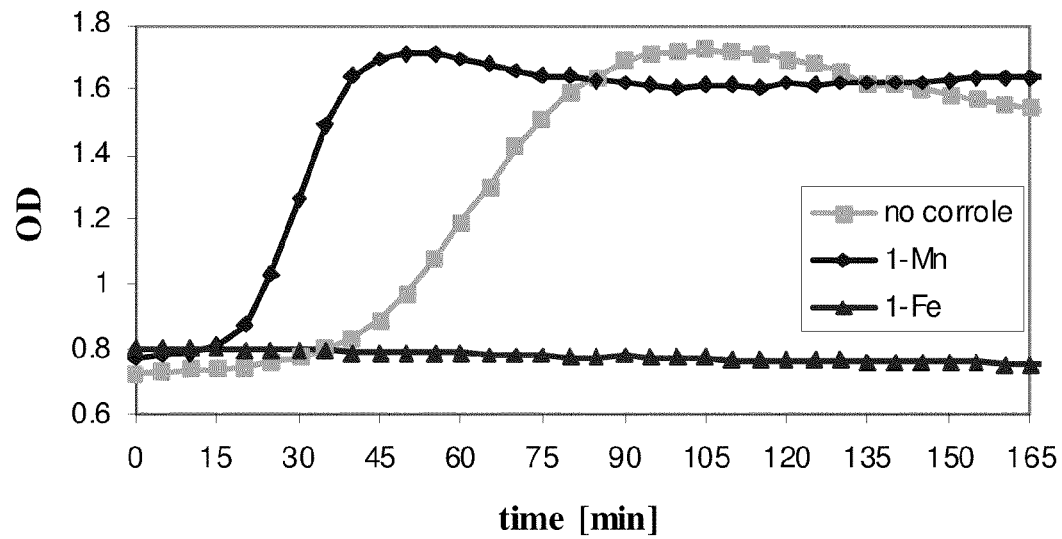
FIGS. 3A-3D depict the effect of corrole (2.5 μM) on the kinetics of $CuSO_4$-induced (5 μM) oxidation of LDL (100 mg protein/L): 3A) conjugated dienes formation followed at 234 nm; 3B) lipid peroxide formation; and 3C) aldehydes formation followed by thiobarbituric acid reactive substances (TBARS) measurement; 3D) effect of corrole (2.5 μM) on the kinetics of $CuSO_4$-induced (5 μM) oxidation of HDL (100 mg protein/L): conjugated dienes formation followed at 234 nm. ⋯✧⋯ without corrole ⋯♦⋯ with 1-Mn; and ⋯▲⋯ with 1-Fe. MDA—Malonyldialdehyde.
Figure 3B:
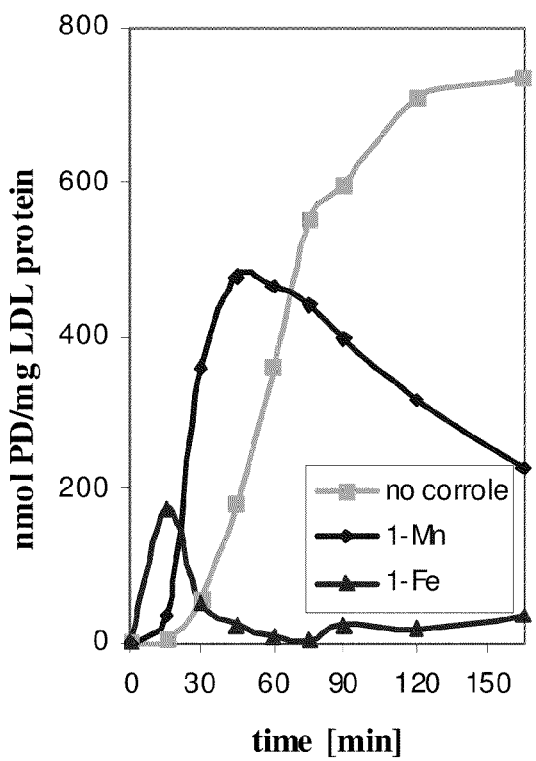
Figure 3C:
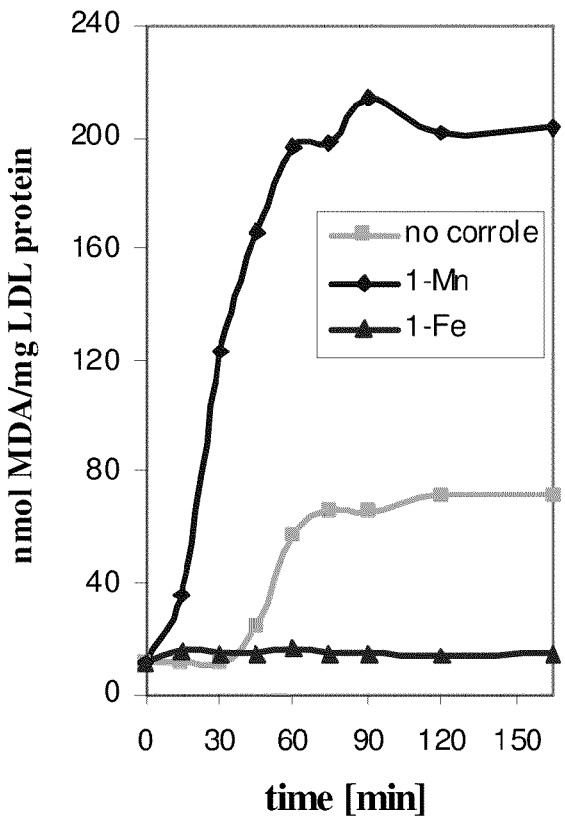

The more commonly used copper-induced LDL oxidation protocol was also applied. Indeed, the aforementioned indications pointing toward pro-oxidant activity of 1-Mn and anti-oxidant activity of 1-Fe gained highly significant supporting evidence from these experiments. This may be appreciated from FIGS. 3A-3C, which show the time course of stepwise formation of conjugated dienes, hydroperoxides, and aldehydes (2.5 µM of metal corrole). Both the rate and the total damage were very much increased by 1-Mn: the delay in formation of conjugated dienes was shortened from 30 to 15 minutes and both hydroperoxides and aldehydes were formed with almost no delay time. The total amount of hydroperoxides rapidly reached a maximum at 45 min (due to its subsequent transformation to the final aldehyde products) and the total concentration of aldehydes was increased by a factor of 3 relative to the control experiment. Most important, the effect of 1-Fe was dramatically different: practically no damage was noticed by all three criteria. Even after 24 hours no aldehydes were formed in the presence of 1-Fe, proving it to be a catalytic anti-oxidant, as appose to the natural anti-oxidants that only delay the oxidation. Similar results were obtained for HDL oxidation.

Figure 4A:
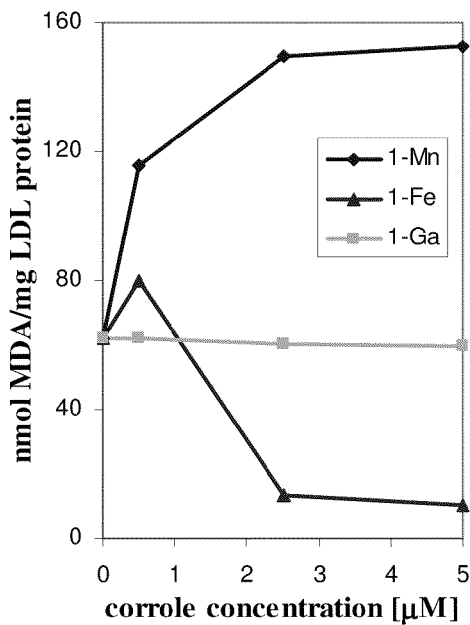
FIG. 4A-4B show the dependency of $CuSO_4$-induced LDL (4A) or (HDL) (4B) oxidation on the corrole concentration as measured by TBARS formation after 2 hr (for LDL) or 5 hr (for HDL) for various corrole concentrations. LDL or HDL (100 g protein/L) was incubated with the corroles (⋯♦⋯ 1-Mn; ⋯▲⋯ 1-Fe; and ⋯✧⋯ 1-Ga) for 30 min and then $CuSO_4$ (5 μM) was added. TBARS were measured after 2 hr (for LDL) and 5 hr (for HDL).

The dependence of LDL oxidation on the corrole concentration was examined by analyses performed 2 hours after oxidation initiation by the copper ion (FIG. 4A). The manganese complex 1-Mn displayed an increased damage of about 150% up to a concentration of 0.5 µM, with a minor increase thereon. On the contrary, the iron complex 1-Fe caused a minor increase in TBARS at a concentration of 0.5 µM, but resulted in a complete inhibition at concentrations of 2.5 µM and higher. To the best of our knowledge, these results are unmatched by any previously reported metal complexes. To eliminate a possible effect of the corrole macrocycle itself, the gallium complex of 1 (1-Ga) was also examined and found to provide exactly the same results as obtained without any corrole-based additive in all the concentrations examined.

Comparison of the above mentioned results to results obtained with porphyrins (the most efficient complexes reported up to date) shows that the iron corrole is quite superior relative to them. The manganese complexes of pyridinium-substituted porphyrins displayed a pro-oxidative role when LDL was oxidized by peroxynitrite, and shifted to an anti-oxidative role only in the presence of reductants such as uric acid (Trostchansky et al., 2003). Even then, the concentration needed for 100% inhibition of oxidation is 100 µM (Day et al., 1999), 40 fold higher than 1-Fe concentration needed for a full inhibition. In addition, these complexes did not inhibit copper—induced LDL oxidation (Bloodsworth et al., 2000). On the other hand, iron porphyrins did not display potency for inhibiting LDL oxidation at all (Day et al., 1999). It is further interesting to note that hemin, the naturally occurring iron porphyrin, is frequently used for initiation of LDL oxidation rather than its inhibition (Camejo et al., 1998; Kapiotis et al., 2005).

Figure 3D:
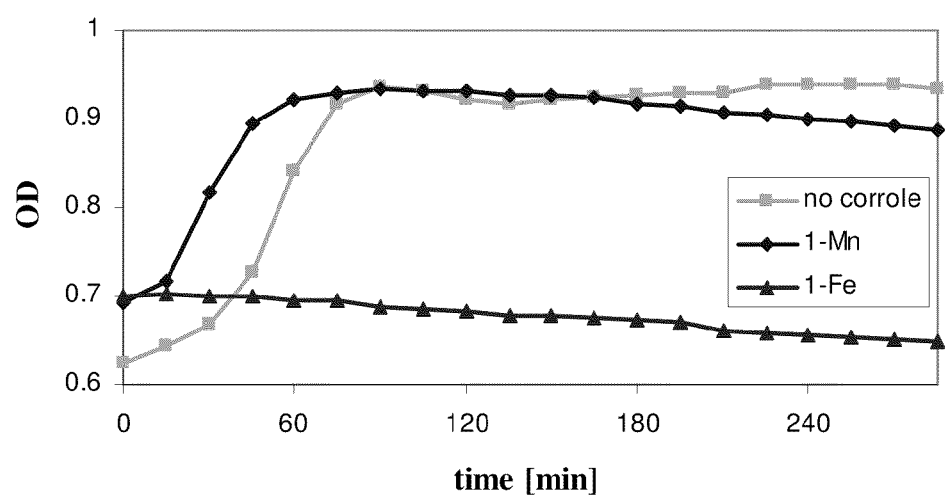
Figure 4B:
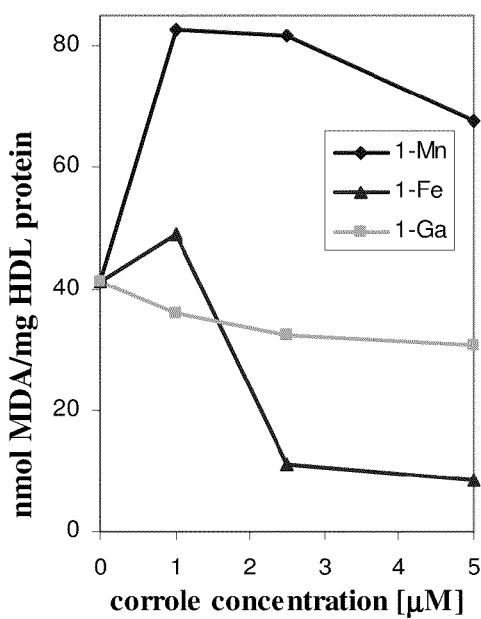

As it was found that in full serum most of the corrole binds to HDL, the effect of corroles on HDL oxidation was also examined. The results for the copper-induced oxidation of HDL were very similar to the results obtained for LDL. 1-Mn was a pro-oxidant, as it shortened the delay time for conjugated dienes formation, while 1-Fe completely eliminated their formation (FIG. 3D). It should be mentioned that the damage measured for HDL is lower than that measured for LDL, due to the lower lipid content of HDL. Analysis of the dependence of oxidation on corrole concentration revealed that 1-Mn increases TBARS formation about 2-folds in all concentrations measured and 1-Fe exhibited its protective effect at concentrations of 2.5 µM and higher than (FIG. 4B), as was also found for LDL.

Example 5

The Corrole Metal Complexes Affect Cholesterol Distribution In Vitro

Examination of the different fractions isolated from the experiments in Example 3 (FIG. 1) further revealed that the amount of cholesterol in LDL from corrole-treated serum was lowered by about 20%, while it was increased in the HDL and LPDS (lipoprotein deficient serum) fractions. This suggests that strong binding of the metallocorroles indeed affects cholesterol distribution. A still further indication for a favorable alteration of cellular cholesterol transport by metallocorroles was obtained by studying cholesterol efflux from J-774 macrophages in a lipoprotein-free medium. The iron complex (but not the manganese and gallium complexes) of corrole 1 increased the cholesterol efflux by up to 20% in a dose-dependent fashion.

Example 6

The Corrole Metal Complexes Affect Cholesterol Metabolism and PON Activity In Vivo Apolipoprotein E deficient mice ($E^0$ mice) are the most common murine model used for atherosclerosis development studies. $E^0$ mice are hypercholesterolemic and develop spontaneous atherosclerotic lesions similar in development and morphology to those in humans.

Figure 5A:
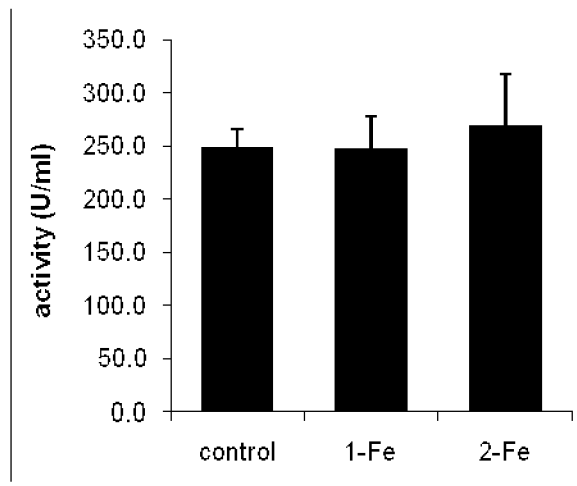
FIGS. 5A-5B show the effect of corrole 1-Fe and 2-Fe consumption by $E^0$ mice on serum arylesterase activity (5A) and on HDL-associated PON activity (5B).
Figure 5B:
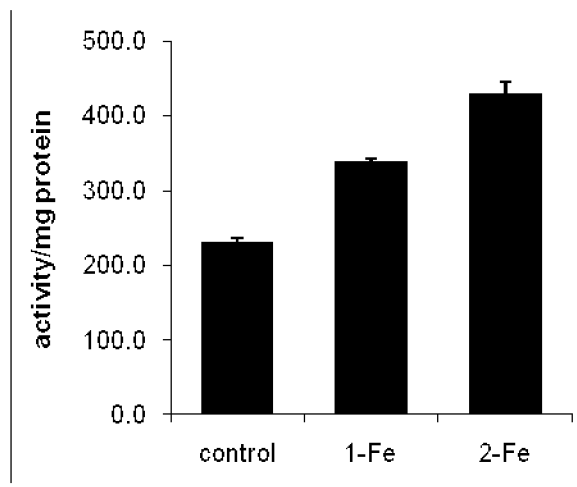
Figure 6A:
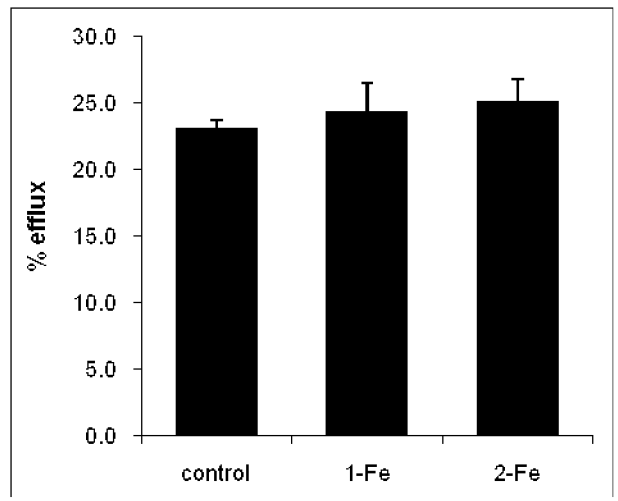
FIGS. 6A-6C show the effect of corrole 1-Fe and 2-Fe consumption by $E^0$ mice on cholesterol efflux and biosynthesis: (6A) serum-mediated efflux from J-774 macrophages; (6B) efflux from the $E^0$ MPM (mouse peritoneal macrophages); (6C) cholesterol synthesis by MPMs.
Figure 6B:
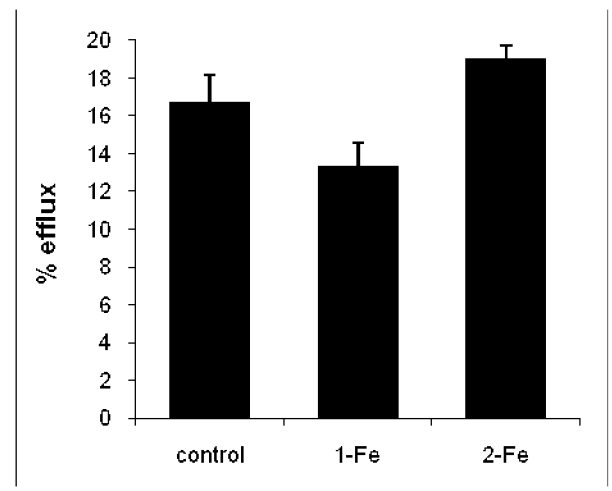
Figure 6C:
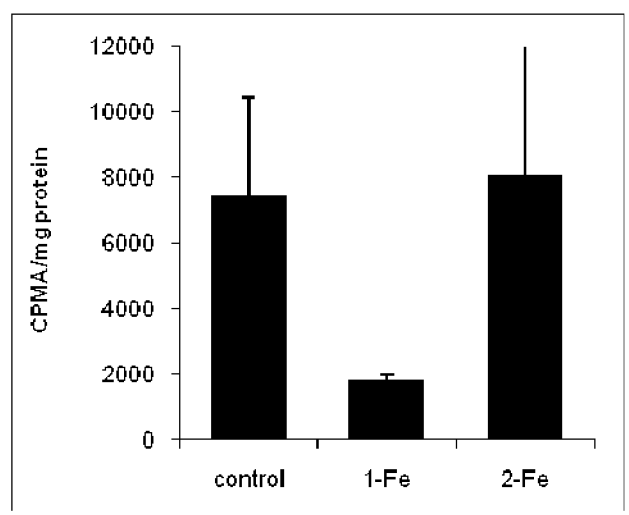

Thirty six $E^0$ mice (about 10 weeks old) were randomly divided into 3 equal groups that differed only in the type of drinking water: i.e. no additive, and water containing 0.04 mM of either 1-Fe or 2-Fe (Scheme 2), respectively (8 mg/Kg/day). The mice were sacrificed after a period of 14 weeks from the start of the experiments. The effect of the corroles on paraoxonase 1 (PON1) was evaluated by measuring arylesterase activity. The corroles had a minor effect on serum arylesterase activity, with 1-Fe showing no effect and 2-Fe showing an 8% increase in activity (FIG. 5A). However, HDL-associated PON activity was highly affected by the corroles, showing an increase of 47% and 86% for 1-Fe and 2-Fe, respectively (FIG. 5B). Further effects of the corroles were on cholesterol efflux and biosynthesis: 1-Fe increased serum-mediated efflux from J-774 macrophages by 7%, and 2-Fe by 9% (FIG. 6A); efflux from the $E^0$ MPM was decreased 20% by 1-Fe but increased 14% by 2-Fe (FIG. 6B); and cholesterol synthesis by MPMs was reduced as much as 76% by 1-Fe whereas 2-Fe increased the synthesis by 8% (FIG. 5C). Taking all these results into account, 2-Fe is superior in all PON1 and cholesterol efflux aspects, but 1-Fe had a major effect on cholesterol synthesis that was not displayed at all by 2-Fe.

Example 7

Figure 7A:
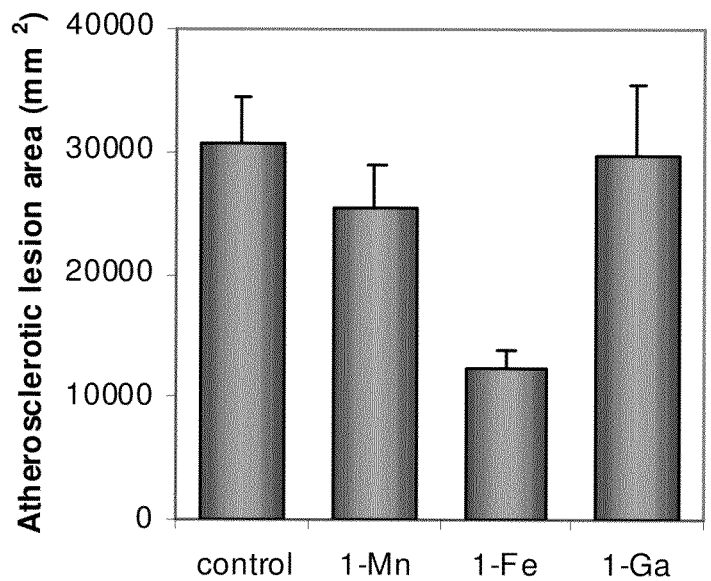
FIGS. 7A-7C show the effect of corrole 1-Mn, 1-Fe and 1-Ga consumption on lesion formation in atherosclerotic $E^0$ mice: (7A) the size of atherosclerotic lesion in the different groups; (7B) a cross-section from the aortic arch of a control mouse; (7C) a cross-section from the aortic arch of a mouse that consumed 1-Fe. The lipid components are stained in a brown-black color, thus highlighting the foam cells.
Figure 7B:
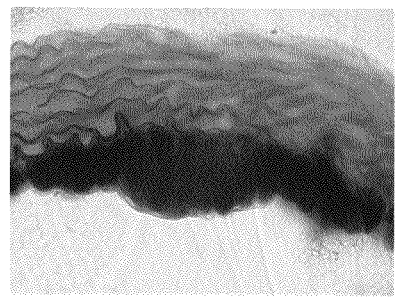
Figure 7C:
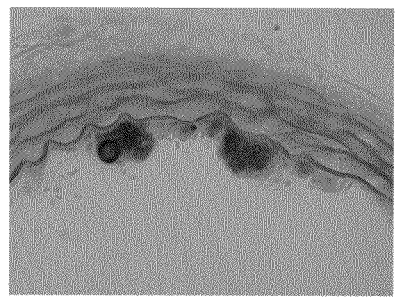

The Corrole Metal Complexes can Prevent Atherosclerosis In Vivo as Well as Reduce Cholesterol Levels and Increase PON2 Activity 24 $E^0$ mice (about 10 weeks old) were randomly divided into 4 equal groups that differed only in the type of drinking water: i.e. no additive, and water containing 0.04 mM of either 1-Mn, 1-Fe, or 1-Ga, respectively. The above dosage of corrole correspond to 0.2 mg per mouse per day; and 1-Ga was included in the study in order to distinguish between a possible role of the corrole macrocycle vs. that of the transition metal ion (iron or manganese) chelated by the corrole. The results obtained from mice that were sacrificed after a period of 10 weeks from the start of the experiments were highly revealing (FIGS. 7A-7C and 8A-8B). The histopathological development of lesions in the aorta was very high for untreated mice (FIGS. 7A-7B) and for those that received 1-Ga. A small but significant decrease of 17% (relative to the control group) in the average lesion area was obtained for the 1-Mn group (despite of the above in vitro indications of a pro-oxidant activity of this complex). One (out of many possible) reason for the apparent contradiction between these in vitro and in vivo investigations could be the inhibition of nitrosative rather than oxidative damage by 1-Mn. Most important, the in vivo results obtained with 1-Fe (FIGS. 7A and 7C) were completely consistent with all other in vitro results and very much out of the range of statistical uncertainty (FIG. 7A). Two of the mice receiving that treatment did actually not develop atherosclerotic lesions at all and the average lesion area for the other four mice was 60% smaller than that obtained for the control mice. These observations are much better than those obtained by other methods, including $E^0$ mice that were treated by natural anti-oxidants (48% reduction when consuming red wine (Hayek et al., 1997; Fuhrman et al., 1995) and 44% for pomegranate juice (Aviram et al., 2000)) or those that were intraperitoneally-treated with different synthetic catalysts for decomposition of reactive oxygen species. In fact, we are not aware of any report where a positive effect of orally administered synthetic anti-oxidants displayed such a positive effect on postponing or eliminating the development of atherosclerosis.

Figure 8A:
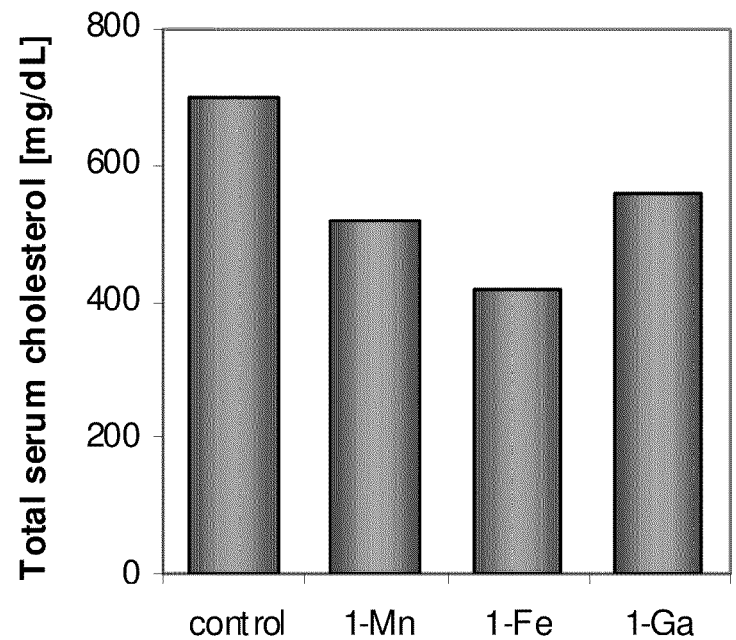
FIGS. 8A-8B show the effect of corrole 1-Mn, 1-Fe and 1-Ga consumption by atherosclerotic $E^0$ mice on serum total cholesterol (8A), and macrophage PON 2 activity (8B).
Figure 8B:
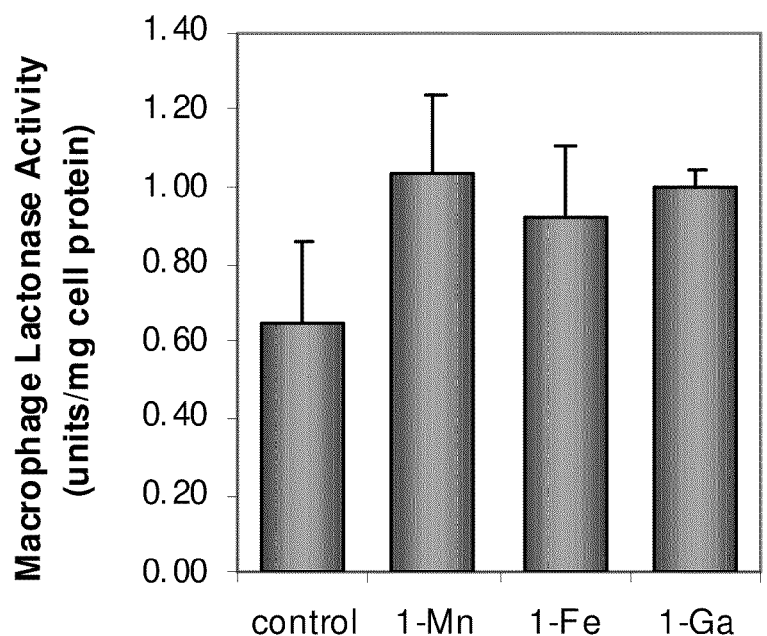

The sacrificed mice were also examined with regard to other factors relevant to the development of atherosclerosis. This identified two parameters that are not related in an obvious fashion to the anti-oxidant activity of the corroles, but may also have contributed to the observed decrease in lesion area: the levels of total serum cholesterol and the macrophage lactonase activity representing cellular paraoxonase 2 (PON2). The former is considered as one of the most common risk factors contributing to atherosclerosis development, while PON2 is an enzyme acting as an antioxidant in the cellular level, as shown in cells overexpressing PON2 which are less able to oxidize LDL (Ng et al., 2001). The total serum cholesterol concentration in mice that received 1-Fe was lower by 40% than that observed in the control group; and significant reductions of 26% and 20% were also noted in mice that received 1-Mn and 1-Ga, respectively (FIG. 8A). Examination of PON2 activity revealed an increase in PON2 lactonase activity versus the control mice in all mice groups receiving corrole derivatives: 41% for 1-Fe, 60% for 1-Mn, and 55% for 1-Ga (FIG. 8B). The combination of low serum cholesterol levels and increased macrophage PON2 lactonase activity may serve as an additional explanation for the positive effect displayed in the in vivo investigations with 1-Mn, despite of the discouraging in vitro results with that corrole.

EXAMPLE

Preparation of 5,10,15-tris(4-methoxy-2,3,5,6-tetrafluorophenyl)-2,17-bis(sulfonic acid)corrolato iron(III) (2-Fe)

(i) Preparation of 5,10,15-tris(4-methoxy-2,3,5,6-tetrafluorophenyl)-corrole 200 mg of 5,10,15-tris(pentafluorophenyl)corrole was dissolved in 100 mL of sodium methoxide solution (0.5 M in methanol). The solution was heated to reflux for 6 hr under argon, followed by evaporation of the solvent. The product was purified by two subsequent silica gel columns (the eluent was ethanol for the first column and $CH_2Cl_2$/n-hexane 2:1 for the second column), affording 160 mg (77% yield) of 5,10,15-tris(4-methoxy-2,3,5,6-tetrafluorophenyl)corrole. $^1$H NMR (300 MHz, $CDCl_3$) δ=9.02 (d, J=4.0 Hz, 2H), 8.73 (d, J=4.8 Hz, 2H), 8.54 (d, J=4.8 Hz, 2H), 8.51 (d, J=4.0 Hz, 2H), 4.31 (s, 9H). $^{19}$F NMR (282.4 MHz, $CDCl_3$) δ=−139.6 (dd, $J^1$=22 Hz, $J^2$=7.0 Hz, 2F), −140.1 (dd, $J^1$=22 Hz, $J^2$=7.0 Hz, 4F), −158.2 (dd, $J^1$=22 Hz, $J^2$=7.0 Hz, 4F), −158.6 (dd, $J^1$=22 Hz, $J^2$=7.0 Hz, 2F); MS (TOF LD-) m/z (%) 832.0 (100%) [M]).

(ii) Preparation of 5,10,15-tris(4-methoxy-2,3,5,6-tetrafluorophenyl)-2,17-bis(sulfonic acid)corrole 100 mg of 5,10,15-tris(4-methoxy-2,3,5,6-tetrafluorophenyl)corrole and 10 ml of sulfuric acid was stirred at 25 C for 4 hr, after which the reaction mixture was cooled by an ice bath and treated with small ice chips (5-10 g). The acid was neutralized by sodium carbonate, and the product was separated from the sodium sulfate via adding ethanol, filtration and evaporation. The product was purified by silica gel column (the eluent was $CH_2Cl_2$/ethanol 2:1), affording 80 mg (67% yield) of 5,10,15-tris(4-methoxy-2,3,5,6-tetrafluorophenyl)-2,17-bis(sulfonic acid)corrole. $^1$H NMR (300 MHz, $CD_3OD$) δ=9.67 (s, 1H), 8.57 (s, 1H), 8.38 (d, J=4.8 Hz, 1H), 8.22 (d, J=4.5 Hz, 1H), 8.15 (d, J=4.8 Hz, 1H), 8.14 (d, J=4.5 Hz, 2H), 4.24 (s, 3H), 4.23 (s, 3H), 4.21 (s, 3H). $^{19}$F NMR (282.4 MHz, $CD_3OD$) δ=−140.9 (dd, $J^1$=24 Hz, $J^2$=8.0 Hz, 2F), −141.9 (dd, $J^1$=24 Hz, $J^2$=8.0 Hz, 2F), −142.1 (dd, $J^1$=24 Hz, $J^2$=8.0 Hz, 2F), −161.6 (dd, $J^1$=24 Hz, $J^2$=8.0 Hz, 2F), −162.1 (dd, $J^1$=24 Hz, $J^2$=8.0 Hz, 2F), −164.3 (dd, $J^1$=24 Hz, $J^2$=8.0 Hz, 2F). MS (TOF LD-) m/z (%) 1011.9 (100%) [$M^{2-}$+$Na^+$]); MS (Electro-spray) m/z (%) 494.90 (100%) [$M^{2-}$/2]).

(iii) Preparation of 5,10,15-tris(4-methoxy-2,3,5,6-tetrafluorophenyl)-2,17-bis(sulfonic acid)corrolato iron(III)

One portion of $FeCl_2.4H_2O$ (100 mg) was added at once to pyridine solution (10 ml) of 2,17-bis-sulfonato-5,10,15-tris (paramethoxytetrafluorophenyl)corrole (100 mg), and the mixture was heated immediately to reflux for 10 min. The product was purified by silica gel column (the eluent was ether/ethanol 3:1 at the beginning then ether/ethanol 1:2), affording 75 mg (71% yield) of 5,10,15-tris(4-methoxy-2,3,5,6-tetrafluorophenyl)-2,17-bis(sulfonic acid)corrolato iron (III). $^{19}$F NMR (282.4 MHz, CD$_3$OD) δ=−109.2 (2F), −119.3 (4F), −153.4 (2F), −154.8 (2F), −157.4 (2F). MS (TOF LD-) m/z (%) 1065.9 (100%) [M$^{2-}$+Na$^+$]; MS (Electro-spray) m/z (%) 521.49 (100%) [M$^{2-}$/2]).

Example 9

Preparation of 5,10,15-tris(4-methoxy-2,3,5,6-tetrafluorophenyl)-2,17-bis(sulfonic acid)corrolato manganese(III) (2-Mn)

A flask loaded with 10 ml of DMF solution of 2,17-bis-sulfonato-5,10,15-tris(paramethoxytetrafluorophenyl)corrole (15 mg) and Mn(OAc)$_2$.4H$_2$O (15 mg) was heated to reflux for 15 min, followed by evaporation of the solvent. The inorganic salts were separated by column chromatography of silica (eluent ether/ethanol 1:1), affording 14 mg (89% yield) of 5,10,15-tris(4-methoxy-2,3,5,6-tetrafluorophenyl)-2,17-bis(sulfonic acid)corrolato manganese(III). $^{19}$F NMR (282.4 MHz, CD$_3$OD) δ=−126 to −135 (broad peak 6F), −158.2 (4F), −161.4 (2F). MS (TOF LD-) m/z (%) 1065.9 (100%) [M$^{2-}$+Na$^+$]; MS (Electro-spray) m/z (%) 520.97 (100%) [M$^{2-}$/2]).

REFERENCES

Aviram, M. (1983) Plasma lipoprotein separation by discontinuous density gradient ultracentrifugation in hyperlipoproteinemic patients. Biochem Med 30, 111-8.

Aviram, M. (1996) Interaction of oxidized low density lipoprotein with macrophages in atherosclerosis, and the antiatherogenicity of antioxidants. Eur J Clin Chem Clin Biochem 34, 599-608.

Aviram, M. (1995) Oxidative modification of low density lipoprotein and its relation to atherosclerosis. Isr J Med Sci 31, 241-9.

Aviram, M., et al. (2000) Pomegranate juice consumption reduces oxidative stress, atherogenic modifications to LDL, and platelet aggregation: studies in humans and in atherosclerotic apolipoprotein E-deficient mice. Am J Clin Nutr 71, 1062-76.

Aviram, M., Vaya, J. and Lester, P. (2001) Markers for low-density lipoprotein oxidation. Methods in Enzymology 335, 244-256.

Barber, S. C., Mead, R. J. and Shaw, P. J. (2006) Oxidative stress in ALS: A mechanism of neurodegeneration and a therapeutic target. Biochimica et Biophysica Acta (BBA)—Molecular Basis of Disease 1762, 1051-1067.

Bartletta, D., Churcha, D. F., Boundsd, P. L. and Koppenol W. H. (1995) The kinetics of the oxidation of L-ascorbic acid by peroxynitrite. Free Rad. Biol. Med. 18, 85-92.

Beal, M. F. (2002) Oxidatively modified proteins in aging and disease. Free Radical Biology and Medicine 32, 797-803.

Bendix, J.; Dmochowski, I. J.; Gray, H. B.; Mahammed, A.; Simkhovich, L.; Gross, Z. (2000) Angew. Chem. Mt. Ed. Eng. 39, 4048.

Bloodsworth, A., et al. (2000) Manganese-porphyrin reactions with lipids and lipoproteins. Free Radic Biol Med 28, 1017-29.

Bonneau, S., Morliere, P. and Brault, D. (2004) Dynamics of interactions of photosensitizers with lipoproteins and membrane-models: correlation with cellular incorporation and subcellular distribution. Biochem Pharmacol 68, 1443-52.

Camejo, G., Halberg, C., Manschik-Lundin, A., Hurt-Camejo, E., Rosengren, B., Olsson, H., Hansson, G. I., Forsberg, G. B. and Ylhen, B. (1998) Hemin binding and oxidation of lipoproteins in serum: mechanisms and effect on the interaction of LDL with human macrophages. J Lipid Res 39, 755-66.

Day, B. J., Batinic-Haberle, I. and Crapo, J. D. (1999) Metalloporphyrins are potent inhibitors of lipid peroxidation. Free Radic Biol Med 26, 730-6.

Dhaliwal, B. S. and Steinbrecher, U. P. (1999) Scavenger receptors and oxidized low density lipoproteins. Clin Chim Acta 286, 191-205.

Esterbauer, H., Striegl, G., Puhl, H. and Rotheneder, M. (1989) Continuous monitoring of in vitro oxidation of human low density lipoprotein. Free Radic Res Commun 6, 67-75.

Esterbauer, H., Rotheneder, M., Striegl, G., Waeg, G., Ashy, A., Sattler, W. and Jurgens G. (1989) Vitamin E and other Lipophilic Antioxidants Protect LDL against Oxidation. Lipid—Fett 91, 316-324.

Ferroni F, Maccaglia A, Pietraforte D, Turco L, Minetti M. (2004) Phenolic antioxidants and the protection of low density lipoprotein from peroxynitrite-mediated oxidations at physiologic CO2. J Agric Food Chem. 52(10): 2866-74.

Fuhrman, B., Lavy, A. and Aviram, M. (1995) Consumption of red wine with meals reduces the susceptibility of human plasma and low-density lipoprotein to lipid peroxidation. Am J Clin Nutr 61, 549-54.

Gershman Z., Goldberg I., Gross Z. (2007) DNA binding and catalytic properties of positively charged corroles. Angew. Chem. Int. Ed. 46, 4320-24.

Griffin E, Re A, Hamel N, Fu C, Bush H, McCaffrey T, Asch A S (2001) A link between diabetes and atherosclerosis: Glucose regulates expression of CD36 at the level of translation. Nat Med 7:840-6

Gross, Z.; Galili, N.; Saltsman, I. (1999) Angew. Chem. Int. Ed. 38, 1427.

Haber A, Agadjanian H, Medina-Kauwe L K, Gross Z. (2008) Corroles that bind with high affinity to both apo and holo transferrin. J Inorg Biochem. 102(3):446-57.

Halliwell, B. and Gutteridge, J. M. C. (1999) Free Radicals in Biology and Medicine. Oxford University Press, Oxford.

Hayek, T., Fuhrman, B., Vaya, J., Rosenblat, M., Belinky, P., Coleman, R., Elis, A. and Aviram, M. (1997) Reduced Progression of Atherosclerosis in Apolipoprotein E-Deficient Mice Following Consumption of Red Wine, or Its Polyphenols Quercetin or Catechin, Is Associated With Reduced Susceptibility of LDL to Oxidation and Aggregation. Arterioscler Thromb Vasc Biol 17, 2744-2752.

Hunt, J. A., Lee, J. and Groves, J. T. (1997) Amphiphilic peroxynitrite decomposition catalysts in liposomal assemblies. Chemistry & Biology 4, 845-858.

Kapiotis, S., Hermann, M., Exner, M., Laggner, H., and Gmeiner, B. M. (2005) Copper- and magnesium protoporphyrin complexes inhibit oxidative modification of LDL induced by hemin, transition metal ions and tyrosyl radicals. Free Radic Res 39, 1193-202.

Lowry, O. H., Rosebrough, N. J., Farr, A. L. and Randall, R. J. (1951) Protein measurement with the Folin phenol reagent. J Biol Chem 193, 265-75.

Mahammed, A., Gray, H. B., Weaver, J. J., Sorasaenee, K. and Gross, Z. (2004) Amphiphilic corroles bind tightly to human serum albumin. Bioconjug Chem. 15, 738-46.

Mahammed, A. and Gross, Z. (2005) Albumin-conjugated corrole metal complexes: extremely simple yet very efficient biomimetic oxidation systems. J Am Chem Soc 127, 2883-7.

Mahammed, A. and Gross, Z. (2006) Iron and manganese corroles are potent catalysts for the decomposition of peroxynitrite. Angew Chem Int Ed Engl 45, 6544-7.

Moreira P. I., Siedlak S. L., Aliev G., Zhu X., Cash A. D., Smith M. A. and Perry G. (2005) Oxidative stress mechanisms and potential therapeutics in Alzheimer disease. Journal of Neural Transmission 112, 921-932.

Ng, C. J., Wadleigh, D. J., Gangopadhyay, A., Hama, S., Grijalva, V. R., Navab, M., Fogelman, A. M. and Reddy, S. T. (2001) Paraoxonase-2 is a ubiquitously expressed protein with antioxidant properties and is capable of preventing cell-mediated oxidative modification of low density lipoprotein. J Biol Chem 276, 44444-9.

Rosenblat, M., Draganov, D., Watson, C. E., Bisgaier, C. L., La Du, B. N. and Aviram, M. (2003) Mouse macrophage paraoxonase 2 activity is increased whereas cellular paraoxonase 3 activity is decreased under oxidative stress. Arterioscler Thromb Vasc Biol 23, 468-74.

Saltsman, I., Mahammed, A., Goldberg, I., Tkachenko, E., Botoshansky, M. and Gross, Z. (2002) Selective substitution of corroles: Nitration, hydroformylation, and chlorosulfonation. Journal of the American Chemical Society 124, 7411-7420.

Steinberg, D., Parthasarathy, S., Carew, T. E., Khoo, J. C. and Witztum, J. L. (1989) Beyond cholesterol. Modifications of low-density lipoprotein that increase its atherogenicity. N Engl J Med 320, 915-24.

Stocker, R. and Keaney, J. F. (2005) New insights on oxidative stress in the artery wall. Journal of Thrombosis and Haemostasis. 3, 1825-1834.

Szabó, C., Ischiropoulos, H. and Radi R. (2007) Peroxynitrite: biochemistry, pathophysiology and development of therapeutics. Nat Rev Drug Discov. 6, 662-680.

Thomas, S. R., Davies, M. J. and Stocker R. (1998) Oxidation and Antioxidation of Human Low-Density Lipoprotein and Plasma Exposed to 3-Morpholinosydnonimine and Reagent Peroxynitrite. Chem Res Toxicol 11, 484-494.

Trostchansky, A., Ferrer-Sueta, G., Batthyany, C., Botti, H., Batinic-Haberle, I., Radi, R. and Rubbo, H. (2003) Peroxynitrite flux-mediated LDL oxidation is inhibited by manganese porphyrins in the presence of uric acid. Free Radic Biol Med 35, 1293-300.

Tzulker, R., Glazer, I., Bar-Ilan, I., Holland, D., Aviram, M., Amir, R. (2007) Antioxidant activity, polyphenol content, and related compounds in different fruit juices and homogenates prepared from 29 different pomegranate accessions. J Agric Food Chem. 55(23), 9559-70.

Scheme 1. Some corroles used in the present invention

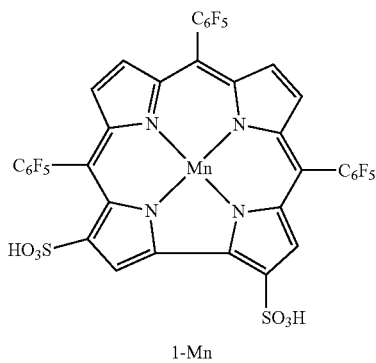

1-Mn

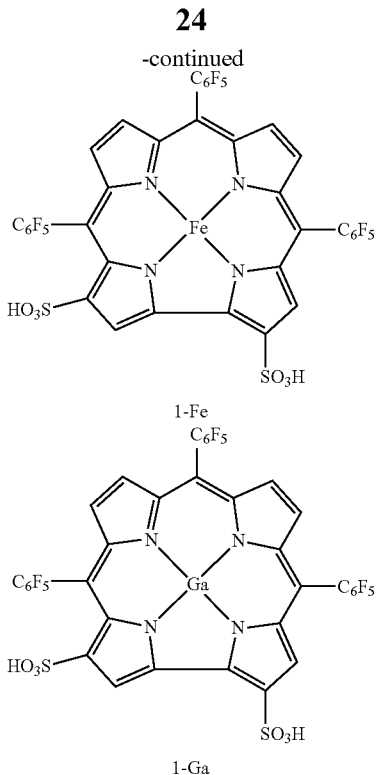

1-Fe

1-Ga

Scheme 2. The disproportionation mechanism for 1-Mn decomposition of hydrogen peroxide and peroxynitrite.

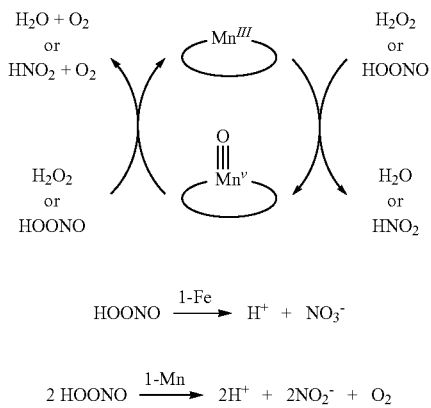

1)

2) $2 \text{ HOONO} \xrightarrow{\text{1-Mn}} 2\text{H}^+ + 2\text{NO}_2^- + \text{O}_2$ $\text{HOONO} \xrightarrow{\text{1-Fe}} \text{H}^+ + \text{NO}_3^-$

The invention claimed is:

1. A method for prevention of atherosclerosis in a subject susceptible to develop atherosclerosis which comprises administering to the subject a prophylactically effective amount of a transition metal complex of an amphiphilic/bipolar corrole selected from the group consisting of 5,10,15-tris(pentafluorophenyl)-2,17-bis(sulfonic acid)-corrolato manganese(III) and 5,10,15-tris(pentafluorophenyl)-2,17-bis(sulfonic acid)-corrolato iron(III), an optically active isomer or a pharmaceutically acceptable salt thereof, said complex having prophylactic activity against atherosclerosis.

2. The method according to claim 1, wherein the transition metal complex of said amphiphilic/bipolar corrole attenuates the formation of atherosclerotic lesions.

3. The method according to claim 1, wherein said transition metal complex of an amphiphilic/bipolar corrole is 5,10,15-tris(pentafluorophenyl)-2,17-bis(sulfonic acid)-corrolato manganese(III).

4. The method according to claim 1, wherein said transition metal complex of an amphiphilic/bipolar corrole is 5,10,15-tris(pentafluorophenyl)-2,17-bis(sulfonic acid)-corrolato iron(III).

5. A method for reducing blood cholesterol comprising administering to a subject susceptible to development of atherosclerosis an effective amount of a transition metal complex of an amphiphilic/bipolar corrole selected from the group consisting of 5,10,15-tris(pentafluorophenyl)-2,17-bis(sulfonic acid)-corrolato manganese(III) and 5,10,15-tris(pentafluorophenyl)-2,17-bis(sulfonic acid)-corrolato iron (III), an optically active isomer, or a pharmaceutically acceptable salt thereof.

6. A method for reducing oxidation or nitration of low-density lipoproteins (LDL), high-density lipoproteins (HDL), or both, comprising administering to a subject susceptible to development of atherosclerosis an effective amount of a transition metal complex of an amphiphilic/bipolar corrole selected from the group consisting of 5,10,15-tris(pentafluorophenyl)-2,17-bis(sulfonic acid)-corrolato manganese(III) and 5,10,15-tris(pentafluorophenyl)-2,17-bis(sulfonic acid)-corrolato iron(III), an optically active isomer, or a pharmaceutically acceptable salt thereof.

7. The method according to claim 1, wherein said transition metal complex of an amphiphilic/bipolar corrole or a pharmaceutically acceptable salt thereof is administered orally.

8. The method of claim 1, wherein said prevention of atherosclerosis is at least in part attributable to reduction of blood cholesterol.

9. The method of claim 1, wherein said prevention of atherosclerosis is at least in part attributable to reduction of oxidation or nitration of low density lipoprotein (LDL), high density lipoprotein (HDL), or both.

* * * * *